(12) United States Patent
Pu et al.

(10) Patent No.: US 8,816,086 B2
(45) Date of Patent: Aug. 26, 2014

(54) PROCESS FOR PREPARING CANNABINOID RECEPTOR LIGANDS

(75) Inventors: Yu-Ming Pu, Gurnee, IL (US); Alan Christesen, Round Lake, IL (US); Steven Cullen, Lake Villa, FL (US); Yi-Yin Ku, Buffalo Grove, IL (US)

(73) Assignee: AbbVie Inc., North Chicago, IL (US)

( * ) Notice: Subject to any disclaimer, the term of this patent is extended or adjusted under 35 U.S.C. 154(b) by 243 days.

(21) Appl. No.: 12/969,047

(22) Filed: Dec. 15, 2010

(65) Prior Publication Data

US 2011/0144343 A1   Jun. 16, 2011

Related U.S. Application Data

(60) Provisional application No. 61/286,850, filed on Dec. 16, 2009.

(51) Int. Cl.
*C07D 513/04* (2006.01)
*A61K 31/4365* (2006.01)

(52) U.S. Cl.
USPC .......................................... 546/114; 514/301

(58) Field of Classification Search
USPC .......................................... 546/114; 514/301
See application file for complete search history.

(56) References Cited

FOREIGN PATENT DOCUMENTS

WO    WO 2007140385 A2 * 12/2007 ........... C07D 277/46
WO    WO2010071783 A1    6/2010

OTHER PUBLICATIONS

Cross, L.C. et al., "IUPAC Commission on Nomenclature of Organic Chemistry: Rules for the Nomenclature of Organic Chemistry, Section E: Stereochemistry," Pure and Applied Chemistry, 1976, vol. 45, pp. 13-30.
Greene, T.W., et al., Protective Groups in Organic Synthesis, 3rd Edition, John Wiley and Sons, Inc., 1999, Table of Contents.
International Search Report for Application No. PCT/US2010/060499, mailed on Feb. 24, 2011, 3 pages.
Shen G., et al., "Synthesis of N-Substituted-2-Aminobenzothiazoles by Ligand-Free Copper(I)-Catalyzed Cross-Coupling Reaction of 2-Haloanilines with Isothiocyanates," European Journal of Organic Chemistry, 2009, pp. 5897-5901.

* cited by examiner

*Primary Examiner* — David K O Dell
(74) *Attorney, Agent, or Firm* — Lisa V. Mueller; Michael Best & Friedrich LLP

(57) ABSTRACT

A process for the preparation of compounds of formula (I) or a salt thereof

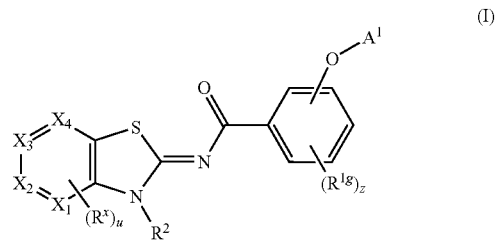

wherein $X_1$, $X_2$, $X_3$, $X_4$, $R^x$, u, $R^2$, $R^{1g}$, z, and $A^1$ are as defined in the specification is disclosed.

18 Claims, No Drawings

PROCESS FOR PREPARING CANNABINOID RECEPTOR LIGANDS

CROSS REFERENCE SECTION TO RELATED APPLICATIONS

This application claims priority to U.S. Application Ser. No. 61/286,850, filed Dec. 16, 2009, and is incorporated herein by reference in its entirety.

TECHNICAL FIELD OF THE INVENTION

A process is provided for preparing fused thiazolidene derivatives and salts thereof. These compounds have activities as Cannabinoid (CB) Receptor ligands.

BACKGROUND OF THE INVENTION

Fused thiazolidene derivatives of formula (I), particularly thiazolo-pyridinylidene compounds have demonstrated activity as Cannabinoid (CB) Receptor ligands, more particularly as selective $CB_2$ receptor ligands. Such ligands provide useful compounds for pharmaceutical products. For example, $CB_2$ receptor ligands can be used for treatment of disorders or conditions related pain such as, but not limited to, chronic pain, neuropathic pain, nociceptive pain, osteoarthritic pain, inflammatory pain, cancer pain, lower back pain, post operative pain, and eye pain; inflammatory disorders, immune disorders, neurological disorders, cancers of the immune system, respiratory disorders, obesity, diabetes, cardiovascular disorders, or for providing neuroprotection.

Previous processes for preparing compounds of formula (I) generally involved a three-step reaction:
(a) coupling of thiazolopyridine-2-amine with a substituted 2-fluorobenzoic acid;
(b) alkylation of the resulting benzamide from step (a) with alkyl halide in the presence of potassium carbonate, under biphasic reaction conditions; and
(c) displacing the fluoride with an appropriate un-protected diol.

While these processes were able to provide analogs of sufficient quantity of compounds of formula (I), and particularly the thiazolo-pyridinylidene analogs for SAR (structural activity relationship) study, the overall low yields of the procedures do not have utility for large scale synthesis. Thus it would be beneficial to provide efficient processes for preparing such compounds of increasing reaction product yield.

SUMMARY OF THE INVENTION

In one aspect, the invention relates to a process for preparing compounds of formula (I)

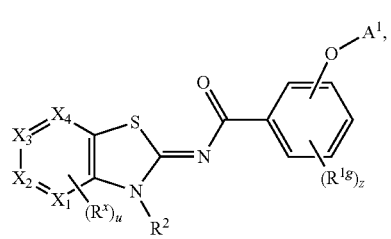

(I)

or salts thereof, wherein $R^{1g}$, at each occurrence, is each independently chosen from the group consisting of $G^{1d}$, $C_1$-$C_4$ alkyl, $C_2$-$C_4$ alkenyl, $C_2$-$C_4$ alkynyl, halogen, $C_1$-$C_4$ haloalkyl, —CN, —$OR^f$, —$OC(O)R^f$, —$OC(O)N(R^f)_2$, —$S(O)_2R^e$, —$S(O)_2N(R^f)_2$, —$C(O)R^f$, —$C(O)OR^f$, —$C(O)N(R^f)_2$, —$N(R^f)_2$, —$N(R^f)C(O)R^f$, —$N(R^f)S(O)_2R^e$, —$N(R^f)C(O)O(R^e)$, —$N(R^f)C(O)N(R^f)_2$, —$(CR^{1c}R^{1d})_{q3}$—$OR^f$, —$(CR^{1c}R^{1d})_{q3}$—$OC(O)R^f$, —$(CR^{1c}R^{1d})_{q3}$—$OC(O)N(R^f)_2$, —$(CR^{1c}R^{1d})_{q3}$—$S(O)_2R^e$, —$(CR^{1c}R^{1d})_{q3}$—$S(O)_2N(R^f)_2$, —$(CR^{1c}R^{1d})_{q3}$—$C(O)R^f$, —$(CR^{1c}R^{1d})_{q3}$—$C(O)OR^f$, —$(CR^{1c}R^{1d})_{q3}$—$C(O)N(R^f)_2$, —$(CR^{1c}R^{1d})_{q3}$—$N(R^f)_2$, —$(CR^{1c}R^{1d})_{q3}$—$N(R^f)C(O)R^f$, —$(CR^{1c}R^{1d})_{q3}$—$N(R^f)S(O)_2R^e$, —$(CR^{1c}R^{1d})_{q3}$—$N(R^f)C(O)O(R^e)$, —$(CR^{1c}R^{1d})_{q3}$—$N(R^f)C(O)N(R^f)_2$, and —$(CR^{1c}R^{1d})_{q3}$—CN;

$R^e$, at each occurrence, is independently $C_1$-$C_4$ alkyl, $C_1$-$C_4$ haloalkyl, monocyclic cycloalkyl, or —$(CR^{1c}R^{1d})_{q3}$-(monocyclic cycloalkyl);

$R^f$, at each occurrence, is independently hydrogen, $C_1$-$C_4$ alkyl, $C_1$-$C_4$ haloalkyl, —$(CR^{1c}R^{1d})_{q3}$—$OR^g$, monocyclic cycloalkyl, or —$(CR^{1c}R^{1d})_{q3}$-(monocyclic cycloalkyl);

$R^g$, at each occurrence, is independently hydrogen, $C_1$-$C_4$ alkyl, $C_1$-$C_4$ haloalkyl, monocyclic cycloalkyl, or —$(CR^{1c}R^{1d})_{q3}$-(monocyclic cycloalkyl);

$A^1$ is —$(CR^{1a}R^{1b})_{q1}$—OH or $A^2$ wherein $A^2$ is $N(R^b)(R^c)$, $G^{1c}$, or —$(CR^{1a}R^{1b})_q$-$G^{1c}$;

$G^{1c}$ is a monocyclic heterocycle or a monocyclic cycloalkyl wherein each ring is optionally substituted with 1, 2, 3, or 4 substituents independently selected from the group consisting of oxo, alkyl, alkenyl, alkynyl, halogen, haloalkyl, —CN, alkoxy, haloalkoxy, —C(O)OH, and —C(O)O(alkyl).

$R^2$ is $C_2$-$C_{10}$ alkyl, alkenyl, alkynyl, haloalkyl, —$(CR^{2a}R^{2b})_{q4}$—O—$R^a$, —$(CR^{2a}R^{2b})_{q4}$—O-$G^{2a}$, —$(CR^{2a}R^{2b})_{q4}$—O—$(CR^{2c}R^{2d})_{q5}$-$G^{2a}$, —$(CR^{2a}R^{2b})_{q5}$—C(O)—$R^a$, —$(CR^{2a}R^{2b})_{q5}$—C(=N—$OR^e$)$R^a$, —$(CR^{2a}R^{2b})_{q5}$—$SO_2$—$R^d$, —$(CR^{2a}R^{2b})_{q5}$-$G^{2a}$, —$(CR^{2a}R^{2b})_{q5}$—C(O)N($R^b$)($R^c$), —$(CR^{2a}R^{2b})_{q4}$—OC(O)N($R^b$)($R^c$), or —$(CR^{2a}R^{2b})_{q5}$—CN;

$G^{2a}$, at each occurrence, is independently cycloalkyl, cycloalkenyl, heterocycle, aryl, or heteroaryl; wherein each of the rings as represented by $G^{2a}$ is optionally substituted with 1, 2, 3, 4, or 5 substituents independently selected from the group consisting of oxo, alkyl, halogen, hydroxy, alkoxy, haloalkoxy, and haloalkyl;

$R^a$ and $R^c$, at each occurrence, are each independently hydrogen, alkyl, haloalkyl, —$(CR^{1a}R^{1b})_{q2}$—$OR^h$, —$(CR^{1a}R^{1b})_{q2}$—$N(R^h)_2$, $G_{1d}$, or —$(CR^{1a}R^{1b})_{q2}$-$G^{1d}$;

$R^b$, at each occurrence, is independently hydrogen, alkyl, haloalkyl, alkoxyalkyl, monocyclic cycloalkyl, —$(CR^{1c}R^{1d})_{q2}$-(monocyclic cycloalkyl), or haloalkoxyalkyl;

$R^d$, at each occurrence, is independently alkyl, haloalkyl, —$(CR^{1a}R^{1b})_{q2}$—$OR^h$, —$(CR^{1a}R^{1b})_{q2}$—$N(R^h)_2$, $G^{1d}$, or —$(CR^{1a}R^{1b})_{q2}$-$G^{1d}$;

$G^{1d}$, at each occurrence, is independently a monocyclic heterocycle, a monocyclic heteroaryl, a phenyl, a monocyclic cycloalkyl, or a monocyclic cycloalkenyl; each of which is optionally substituted with 1, 2, 3, or 4 substituents independently selected from the group consisting of —$N(R^h)_2$, —CN, oxo, alkyl, haloalkyl, alkoxy, haloalkoxy, halogen, and hydroxy;

$R^h$, at each occurrence, is independently hydrogen, $C_1$-$C_4$ alkyl, $C_1$-$C_4$ haloalkyl, monocyclic cycloalkyl, or —$(CR^{1c}R^{1d})_{q3}$-(monocyclic cycloalkyl)

wherein the monocyclic cycloalkyl, as a substituent or part of a substituent, of $R^b$, $R^e$, $R^f$, $R^g$, and $R^h$, at each occurrence, is independently unsubstituted are substituted with 1, 2, 3, or 4 substituents independently selected from the group consisting of $C_1$-$C_4$ alkyl, halogen, oxo, hydroxy, $C_1$-$C_4$ alkoxy, $C_1$-$C_4$ haloalkoxy, and $C_1$-$C_4$ haloalkyl;

q, q1 and q2, at each occurrence, are each independently 1, 2, 3, or 4;

$R^{1a}$, $R^{1b}$, $R^{1c}$, $R^{1d}$, $R^{2a}$, $R^{2b}$, $R^{2c}$, and $R^{2d}$, at each occurrence, are each independently hydrogen, halogen, $C_1$-$C_4$ alkyl, or $C_1$-$C_4$ haloalkyl;

q3, at each occurrence, is independently 1, 2 or, 3;
q4, at each occurrence, is independently 2, 3, 4, or 5;
q5, at each occurrence, is independently 1, 2, 3, 4, 5, or 6;
z is 0, 1, 2, 3, or 4;
one of $X_1$, $X_2$, $X_3$, and $X_4$ is N and the others are CH;
u is 0, 1, 2, or 3; and
each $R^x$ is an optional substituent on any substitutable carbon atom, and is independently selected from the group consisting of alkyl, halogen, hydroxy, alkoxy, haloalkoxy, and haloalkyl.

The process comprising the steps of
(1a) treating compounds of formula (IV)

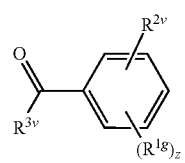

(IV)

wherein $R^{2v}$ is halogen or sulfonate; and $R^{3v}$ is halogen or OH; with a thiocyanate source to produce compounds of formula (V)

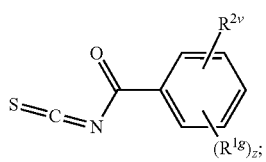

(V)

(1b) reacting compounds of formula (V) with compounds of formula (VI)

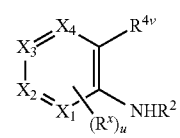

(VI)

wherein $R^{4v}$ is halogen or sulfonate to produce compounds of formula (II) or salts thereof

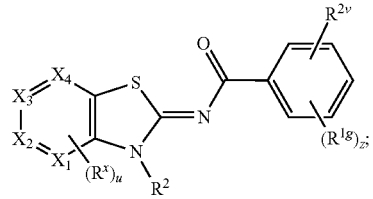

(II)

(2a) treating compounds of formula (II) or salts thereof with compounds of formula HO—$(CR^{1a}R^{1b})_{q1}$—O—$R^p$ or HO-$A^2$; or salts thereof, wherein
$A^2$ is $N(R^b)(R^c)$, $G^{1c}$, or —$(CR^{1a}R^{1b})_q$-$G^{1c}$; and
$R^p$ is hydrogen or a hydroxy-protecting group; to produce compounds of formula (IIIa) or (IIIb) respectively, or salts thereof

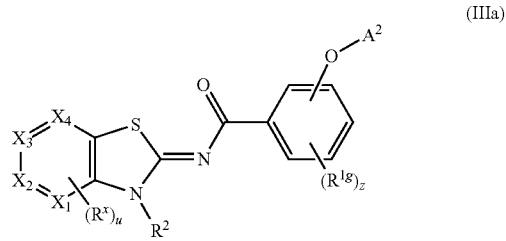

(IIIa)

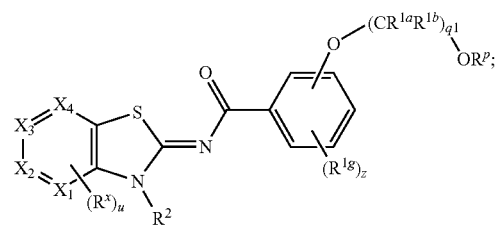

(IIIb)

and
(2b) deprotect compounds of formula (IIIb) or salts thereof wherein $R^p$ is a hydroxy-protecting group to form compounds of formula (Ib) or salts thereof

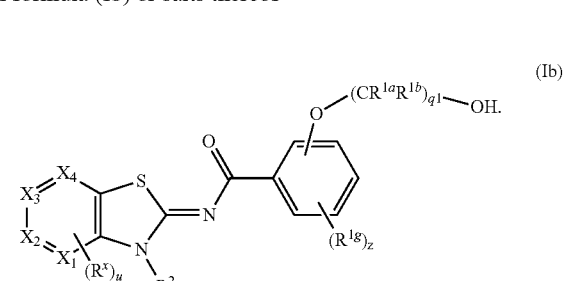

(Ib)

DETAILED DESCRIPTION OF THE INVENTION

A process for preparing compounds of formula (I)

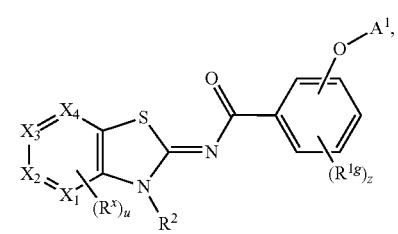

(I)

or salts thereof wherein $A^1$, $X_1$, $X_2$, $X_3$, $X_4$, $R^x$, u, $R^2$, $R^{1g}$, and z are as defined above in the Summary and below in the Detailed Description are disclosed.

In various embodiments, compounds described herein can contain variables that occur more than one time in any substituent or in the compound described or any other formulae herein. Definition of a variable on each occurrence is independent of its definition at another occurrence. Further, combinations of variables are permissible only if such combinations result in stable compounds. Stable compounds are compounds that can be isolated from a reaction mixture.

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond. The term "$C_2$-$C_4$ alkenyl" means an alkenyl group containing 2-4 carbon atoms. Non-limiting examples of alkenyl include buta-2,3-dienyl, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" means a divalent group derived from a straight or branched chain hydrocarbon of 2 to 4 carbon atoms and contains at least one carbon-carbon double. Representative examples of alkenylene include, but are not limited to, —CH═CH— and —CH$_2$CH═CH—.

The term "alkoxy" as used herein, means an alkyl group, as defined herein, appended to the parent molecular moiety through an oxygen atom. The term "$C_1$-$C_4$ alkoxy" as used herein, means a $C_1$-$C_4$ alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkyl" as used herein, means an alkoxy group, as defined herein, appended to the parent molecular moiety through an alkylene group, as defined herein. Non-limiting examples of alkoxyalkyl include tert-butoxymethyl, 2-ethoxyethyl, 2-methoxyethyl, and methoxymethyl.

The term "alkyl" as used herein, means a straight or branched, saturated hydrocarbon chain containing from 1 to 10 carbon atoms. The term "$C_x$-$C_y$ alkyl" means a straight or branched, saturated hydrocarbon chain containing x to y carbon atoms. For example "$C_2$-$C_{10}$ alkyl" means a straight or branched, saturated hydrocarbon chain containing 2 to 10 carbon atoms. For example "$C_1$-$C_4$ alkyl" means a straight or branched, saturated hydrocarbon chain containing 1 to 4 carbon atoms. Examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" means a divalent group derived from a straight or branched, saturated hydrocarbon chain of 1 to 10 carbon atoms, for example, of 1 to 4 carbon atoms. Examples of alkylene include, but are not limited to, —CH$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" as used herein, means a straight or branched hydrocarbon chain containing from 2 to 10 carbon atoms and containing at least one carbon-carbon triple bond. The term "$C_2$-$C_4$ alkynyl" means an alkynyl group containing from 2 to 4 carbon atoms. Representative examples of alkynyl include, but are not limited, to acetylenyl, 1-propynyl, 2-propynyl, 3-butynyl, 2-pentynyl, and 1-butynyl.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Non-limiting examples of the aryl groups include dihydroindenyl, indenyl, naphthyl, dihydronaphthalenyl, and tetrahydronaphthalenyl. The aryl groups can be unsubstituted or substituted, and the bicyclic aryl is attached to the parent molecular moiety through any substitutable carbon atom contained within the bicyclic ring system.

The term "cycloalkyl" or "cycloalkane" as used herein, means a monocyclic, a bicyclic, or a tricyclic cycloalkyl. The monocyclic cycloalkyl is a carboxylic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring. Tricyclic cycloalkyls are exemplified by a bicyclic cycloalkyl fused to a monocyclic cycloalkyl. The monocyclic or bicyclic cycloalkyl ring can contain one or two alkylene bridges, each consisting of one, two, or three carbon atoms, each linking two non-adjacent carbon atoms of the ring system. Non-limiting examples of such bridged cycloalkyl ring systems include bicyclo[3.1.1]heptane, bicyclo[2.2.1]heptane, bicyclo[2.2.2]octane, bicyclo[3.2.2]nonane, bicyclo[3.3.1]nonane, bicyclo[4.2.1]nonane, tricyclo[3.3.1.0$^{3,7}$]nonane (octahydro-2,5-methanopentalene or noradamantane), and tricyclo[3.3.1.1$^{3,7}$]decane (adamantane). The monocyclic, bicyclic, and tricyclic cycloalkyls can be unsubstituted or substituted, and are attached to the parent molecular moiety through any substitutable atom contained within the ring system.

The term "cycloalkenyl" or "cycloalkene" as used herein, means a monocyclic or a bicyclic hydrocarbon ring system. The monocyclic cycloalkenyl has four-, five-, six-, seven- or eight carbon atoms and zero heteroatoms. The four-membered ring systems have one double bond, the five- or six-membered ring systems have one or two double bonds, and the seven- or eight-membered ring systems have one, two, or three double bonds. Representative examples of monocyclic cycloalkenyl groups include, but are not limited to, cyclobutenyl, cyclopentenyl, cyclohexenyl, cycloheptenyl, and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group. The monocyclic or bicyclic cycloalkenyl ring can contain one or two alkylene bridges, each consisting of one, two, or three carbon atoms, each linking two non-adjacent carbon atoms of the ring system. Representative examples of the bicyclic cycloalkenyl groups include, but are not limited to, 4,5,6,7-tetrahydro-3aH-indene, octahydronaphthalenyl, and 1,6-dihydro-pentalene. The monocyclic and bicyclic cycloalkenyl can be attached to the parent molecular moiety through any substitutable atom contained within the ring systems, and can be unsubstituted or substituted.

The term "halo" or "halogen" as used herein, means Cl, Br, I, or F.

The term "haloalkyl" as used herein, means an alkyl group, as defined herein, in which one, two, three, four, five or six hydrogen atoms are replaced by halogen. The term "$C_1$-$C_4$ haloalkyl" means a $C_1$-$C_4$ alkyl group, as defined herein, in which one, two, three, four, five or six hydrogen atoms are replaced by halogen. Representative examples of haloalkyl include, but are not limited to, chloromethyl, 2-fluoroethyl, 2,2,2-trifluoroethyl, trifluoromethyl, difluoromethyl, pentafluoroethyl, 2-chloro-3-fluoropentyl, trifluorobutyl (such as, but not limited to, 4,4,4-trifluorobutyl), and trifluoropropyl (such as, but not limited thereto, 3,3,3-trifluoropropyl).

The term "haloalkoxy" as used herein, means an alkoxy group, as defined herein, in which one, two, three, four, five or six hydrogen atoms are replaced by halogen. The term "$C_1$-$C_4$ haloalkoxy" as used herein, means a $C_1$-$C_4$ alkoxy group, as defined herein, in which one, two, three, four, five or six hydrogen atoms are replaced by halogen. Non-limiting examples of haloalkoxy include 2-fluoroethoxy, 2,2,2-trifluoroethoxy, trifluoromethoxy, and difluoromethoxy.

The term "haloalkoxyalkyl" as used herein, means a haloalkoxy group, as defined herein, appended to the parent moiety through an alkylene group, as defined herein.

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two, or three heteroatoms selected from the group consisting of O, N, and S. The six-membered ring contains zero, one, or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Non-limiting examples of monocyclic heterocycles include azetidinyl (including, but not limited thereto, azetidin-2-yl), azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl (including, but not limited thereto, oxetan-2-yl), piperazinyl, piperidinyl, pyranyl, pyrazolinyl, pyrazolidinyl, pyrrolinyl, pyrrolidinyl (including, but not limited thereto, pyrrolidin-1-yl, pyrrolidin-2-yl, pyrrolidin-3-yl), tetrahydrofuranyl (including, but not limited thereto, tetrahydrofuran-3-yl), tetrahydropyranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle. Non-limiting examples of bicyclic heterocycles include benzopyranyl, benzothiopyranyl, 2,3-dihydrobenzofuranyl, 2,3-dihydrobenzothienyl, and 2,3-dihydro-1H-indolyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle. The monocyclic and the bicyclic heterocycles can contain an alkenylene bridge of two, three, or four carbon atoms, or one or two alkylene bridges of 1, 2, 3, or 4 carbon atoms, or combinations thereof, wherein each bridge links two non-adjacent atoms of the ring system. Non-limiting examples of such bridged heterocycles include octahydro-2,5-epoxypentalene, azabicyclo[2.2.1]heptyl (including 2-azabicyclo[2.2.1]hept-2-yl), hexahydro-2H-2,5-methanocyclopenta[b]furan, hexahydro-1H-1,4-methanocyclopenta[c]furan, aza-admantane (1-azatricyclo[3.3.1.1$^{3,7}$]decane), and oxa-adamantane (2-oxatricyclo[3.3.1.1$^{3,7}$]decane). The monocyclic, bicyclic, and tricyclic heterocycles can be unsubstituted or substituted, and are connected to the parent molecular moiety through any substitutable carbon atom or any substitutable nitrogen atom contained within the rings. The nitrogen and sulfur heteroatoms in the heterocycle rings can optionally be oxidized and the nitrogen atoms can optionally be quarternized.

The term "heteroaryl" as used herein, means a monocyclic heteroaryl or a bicyclic heteroaryl. The monocyclic heteroaryl is a five- or six-membered ring. The five-membered ring contains two double bonds. The five membered ring can contain one heteroatom selected from O or S; or one, two, three, or four nitrogen atoms and optionally one oxygen or one sulfur atom. The six-membered ring contains three double bonds and one, two, three or four nitrogen atoms. Representative examples of monocyclic heteroaryl include, but are not limited to, furanyl (including, but not limited thereto, furan-2-yl), imidazolyl (including, but not limited thereto, 1H-imidazol-1-yl), isoxazolyl, isothiazolyl, oxadiazolyl, 1,3-oxazolyl, pyridinyl (e.g. pyridin-4-yl, pyridin-2-yl, pyridin-3-yl), pyridazinyl, pyrimidinyl, pyrazinyl, pyrazolyl, pyrrolyl, tetrazolyl, thiadiazolyl, 1,3-thiazolyl, thienyl (including, but not limited thereto, thien-2-yl, thien-3-yl), triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Non-limiting examples of bicyclic heteroaryl groups include benzofuranyl, benzothienyl, benzoxazolyl, benzimidazolyl, benzoxadiazolyl, 6,7-dihydro-1,3-benzothiazolyl, imidazo[1,2-c]pyridinyl, indazolyl, indolyl, isoindolyl, isoquinolinyl, naphthyridinyl, pyridoimidazolyl, quinolinyl, thiazolo[5,4-b]pyridin-2-yl, thiazolo[5,4-d]pyrimidin-2-yl, and 5,6,7,8-tetrahydroquinolin-5-yl. The monocyclic and bicyclic heteroaryl groups can be substituted or unsubstituted and are connected to the parent molecular moiety through any substitutable carbon atom or any substitutable nitrogen atom contained within the ring systems. The nitrogen and sulfur heteroatoms in the heteroaryl rings can optionally be oxidized and the nitrogen atoms can optionally be quarternized.

The term "heteroatom" as used herein, means a nitrogen, oxygen, or sulfur atom.

The term "hydroxyl" or "hydroxy" means a —OH group.

The term "oxo" as used herein, means a =O group.

The term "alkali metal" means lithium, sodium, and potassium.

The term "hydroxy-protecting group" means a substituent which protects hydroxy groups against undesirable reactions during synthetic procedures. Examples of hydroxy-protecting groups include, but are not limited to, alkoxyalkyl (e.g. methoxymethyl, ethoxyethyl, t-butoxymethyl, and the like), substituted alkoxyalkyl such as 2-(trimethylsilyl)ethoxymethyl, benzyloxymethyl (e.g. p-methoxybenzyloxymethyl, nitrobenzyloxymethyl, and the like), alkoxyalkoxyalkyl such as 2-methoxyethoxymethyl, benzyl, triphenylmethyl, 2,2,2-trichloroethyl, t-butyl, substituted silyl group (e.g. trimethylsilyl, triethylsilyl, dimethylisopropylsilyl, t-butyldimethylsilyl, diphenylmethylsilyl, and the like), methylene acetal, acetonide benzylidene acetal, cyclic ortho esters, cyclic carbonates, and cyclic boronates. Hydroxy-protecting groups are appended onto hydroxy groups by reaction of the compound that contains the hydroxy group with a base, such as triethylamine, and a reagent selected from an alkyl halide, alkyl triflate, trialkylsilyl halide, trialkylsilyl triflate, aryldialkylsilyltriflate, or an alkylchloroformate, $CH_2I_2$, or a dihaloboronate ester, for example with methyliodide, benzyl iodide, triethylsilyltriflate, acetyl chloride, benzylchloride, or dimethylcarbonate. A protecting group also can be appended onto a hydroxy group by reaction of the compound that contains the hydroxy group with acid and an alkyl acetal. In one embodiment, the hydroxy-protecting group is alkoxyalkyl or substituted silyl groups. In yet another embodiment, the hydroxy-protecting group is alkoxyalkyl (e.g. methoxymethyl).

The term "sulfonate" as used herein include aryl sulfonate or alkyl sulfonate, wherein the hydrogen radicals of the alkyl moiety is optionally replaced by halogens, and the aryl moiety is optionally substituted with 1, 2, 3, or 4 alkyl groups. Non-limiting examples include trifluoromethanesulfonate and p-toluenesulfonate.

$A^1$ is as described in the Summary.

In one subset of formula (I) are compounds wherein $A^1$ is $A^2$ and $A^2$ is as described in the Summary, such as those shown in formula (IIIa)

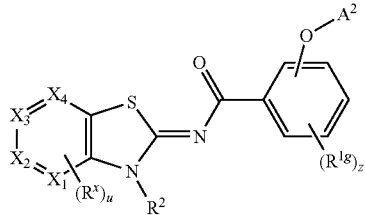

(IIIa)

Examples of compound of formula (I) or (Ma) includes those wherein $A^2$ is $N(R^b)(R^c)$ wherein $R^b$ and $R^c$ are as described in the Summary. In one embodiment, $R^b$ and $R^c$ are the same or different, and are each independently hydrogen or alkyl. In another embodiment, $R^b$ is hydrogen and $R^c$ is alkyl. In yet another embodiment, $R^b$ is hydrogen and $R^c$ is tert-butyl.

Other examples of formula (I) or (Ma) include those wherein $A^2$ is $-(CR^{1a}R^{1b})_q-G^{1c}$ wherein $R^{1a}$, $R^{1b}$, q, and $G^{1c}$ are as defined in the Summary. In one embodiment, $R^{1a}$ and $R^{1b}$ are hydrogen, q is 1 or 2, and $G^{1c}$ is optionally substituted monocyclic heterocycle. In another embodiment, $R^{1a}$ and $R^{1b}$ are hydrogen, q is 1 or 2, and $G^{1c}$ is optionally substituted pyrrolidinyl.

In another subset of formula (I) are compounds wherein $A^1$ is $-(CR^{1a}R^{1b})_{q1}-OH$ and $R^{1a}$, $R^{1b}$, and q1 are as described in the Summary such as those shown in formula (Ib)

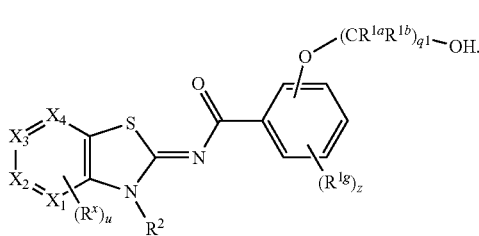

(Ib)

In one embodiment of compounds of formula (I) or (Ib), $R^{1a}$ and $R^{1b}$ are the same or different, and are each independently hydrogen or $C_1-C_4$ alkyl, and q1 is 2, 3, or 4. In another embodiment, $R^{1a}$ and $R^{1b}$ are the same or different, and are each independently hydrogen or alkyl (e.g. methyl), and q1 is 2 or 3. In another embodiment, $R^{1a}$ and $R^{1b}$ are the same or different, and are each independently hydrogen or methyl, and q1 is 2. In certain embodiments, the hydroxy group $-(CR^{1a}R^{1b})_{q1}-OH$ is a secondary or tertiary hydroxy.

Another subset of formula (I) are compounds wherein the $O-A^1$ group is situated at the carbon atom that is adjacent to the carbon atom connected to the carbonyl group, as shown in formula (I-i)

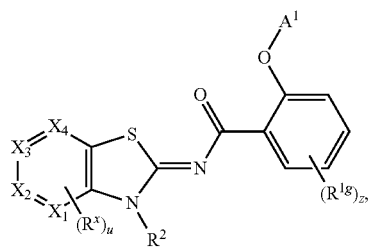

(I-i)

and $X_1$, $X_2$, $X_3$, $X_4$, $A^1$, $R^2$, $R^x$, u, $R^{1g}$, and z have meanings as disclosed in the Summary and the subsets, embodiments, and combinations thereof as described herein above and below.

$X_1$, $X_2$, $X_3$, and $X_4$ have meanings as detailed in the Summary. For example, $X_2$ is N and $X_1$, $X_3$, and $X_4$ are CH; or $X_4$ is N and $X_1$, $X_2$, and $X_3$ are CH.

$R^2$ is as described in the Summary. In certain embodiments, $R^2$ is $C_2-C_{10}$ alkyl (e.g. $C_3-C_4$ alkyl such as but not limited to, isobutyl, n-butyl, n-propyl), alkenyl (e.g. but-2,3-dienyl), alkynyl (e.g. but-3-ynyl), haloalkyl (e.g. 3,3,3-trifluoropropyl, 4,4,4-trifluorobutyl), $-(CR^{2a}R^{2b})_{q4}-O$-haloalkyl, or $-(CR^{2a}R^{2b})_{q5}-G^{2a}$. In certain embodiments, $R^2$ is $C_2-C_{10}$ alkyl (e.g. isobutyl, n-butyl, n-propyl, but not limited thereto), haloalkyl (e.g. 3,3,3-trifluoropropyl, 4,4,4-trifluorobutyl), or $-(CR^{2a}R^{2b})_{q5}-G^{2a}$. In certain embodiments, $R^2$ is $C_2-C_{10}$ alkyl (e.g. isobutyl, n-butyl, n-propyl, but not limited thereto) or haloalkyl (e.g. 3,3,3-trifluoropropyl, 4,4,4-trifluorobutyl). In other embodiments, $R^2$ is $-(CR^{2a}R^{2b})_{q5}-G^{2a}$. In yet other embodiments, $R^2$ is $C_2-C_{10}$ alkyl (e.g. isobutyl, n-butyl, n-propyl, but not limited thereto) or $-(CR^{2a}R^{2b})_{q5}-G^{2a}$. In yet other embodiments, $R^2$ is $C_2-C_{10}$ alkyl (e.g. isobutyl, n-butyl, n-propyl, but not limited thereto). In all these embodiments, $R^{2a}$, $R^{2b}$, q4, q5, and $G^{2a}$ are as described in the Summary and herein. For example, $G^{2a}$ is an optionally substituted monocyclic ring selected from the group consisting of cycloalkyl or heterocycle. In certain embodiments, $G^{2a}$ is an optionally substituted monocyclic cycloalkyl (e.g. cyclopropyl, cyclobutyl, cyclopentyl, but not limited thereto). Each of these rings of $G^{2a}$ is independently unsubstituted or substituted as described in the Summary and herein. For example, each can be unsubstituted or substituted with 1 or 2 groups selected from alkyl such as, but not limited to, $C_1-C_4$ (e.g. methyl), halogen (e.g. F), haloalkyl, oxo, hydroxy, alkoxy (including, but not limited to $OCH_3$), and haloalkoxy. $R^{2a}$ and $R^{2b}$, for example, are each independently hydrogen or $C_1-C_4$ alkyl (e.g. methyl). In certain embodiments, $R^{2a}$ and $R^{2b}$ are hydrogen. q4, for example, is 2 or 3. q5, for example, is 1, 2, or 3. In certain embodiments having $R^2$ is $-(CR^{2a}R^{2b})_{q5}-G^{2a}$, then $R^{2a}$ and $R^{2b}$ are hydrogen and q5 is 1.

$R^{1g}$ and z have values as described generally in the Summary. In certain embodiments, $R^{1g}$ is $C_1-C_4$ alkyl, $C_2-C_4$ alkenyl, $C_2-C_4$ alkynyl, halogen, $C_1-C_4$ haloalkyl, $-CN$, or $-OR^f$ wherein $R^f$ is as disclosed in the Summary. In certain embodiments, $R^{1g}$ is $C_1-C_4$ alkyl, halogen, $C_1-C_4$ haloalkyl (e.g. trifluoromethyl), or $-CN$. In yet other embodiment, $R^{1g}$ is $C_1-C_4$ alkyl, $C_1-C_4$ haloalkyl (e.g. trifluoromethyl), or $-CN$. In certain embodiments, z is 0, 1, or 2. In yet other embodiments, z is 0 or 1. In yet another embodiment, z is 1.

It is appreciated that the present process contemplates synthesis of compounds of formula (I), (IIIa), (Ib), and (I-i) with combinations of the subsets and embodiments described above, including particular, more particular and preferred embodiments.

The present application comprises process for preparing compounds of formula (I), (IIIa), (Ib), and (I-i), suitable for preparing single stereoisomer, for example the "R" or "S" stereoisomers. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30.

The present application also contemplates preparation of various stereoisomers and mixtures thereof of formula (I), (IIIa), (Ib), and (I-i) and is specifically included within the scope of this application. Stereoisomers include enantiomers and diastereomers, and mixtures of enantiomers or diastereomers. Individual stereoisomers can be prepared synthetically from commercially available starting materials which contain asymmetric or chiral centers or by preparation of racemic mixtures followed by resolution which is well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Geometric isomers can exist in the present compounds that are synthesized. Various geometric isomers and mixtures thereof resulting from the disposition of substituents around a carbon-carbon double bond, a carbon-nitrogen double bond, a cycloalkyl group, or a heterocycle group are contemplated. Substituents around a carbon-carbon double bond or a carbon-nitrogen bond are designated as being of Z or E configuration and substituents around a cycloalkyl or a heterocycle are designated as being of cis or trans configuration.

Compounds disclosed herein can exhibit the phenomenon of tautomerism.

Thus, the formulae drawings within this specification can represent only one of the possible tautomeric or stereoisomeric forms. It is to be understood that the invention encompasses any tautomeric or stereoisomeric form, and mixtures thereof, and is not to be limited merely to any one tautomeric or stereoisomeric form utilized within the naming of the compounds or formulae drawings.

The present application provides a process for the preparation of compounds of formula (I) or salts thereof in which $X_1$, $X_2$, $X_3$, $X_4$, $R^2$, $R^x$, u, $R^{1g}$, $R^{1a}$, $R^{1b}$, q1, $A^1$, $A^2$, and z are as disclosed in the Summary and Detailed Description sections; said process comprising (1a) treating compounds of formula (IV)

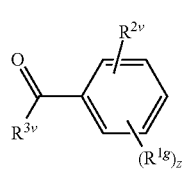

(IV)

wherein $R^{2v}$ is halogen or sulfonate; and $R^{3v}$ is halogen or OH; with a thiocyanate source to produce compounds of formula (V)

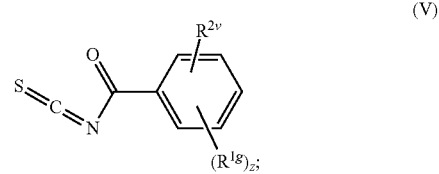

(V)

(1b) reacting compounds of formula (V) with compounds of formula (VI)

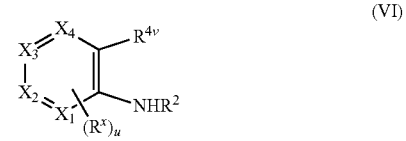

(VI)

wherein $R^{4v}$ is halogen or sulfonate to produce compounds of formula (II) or salts thereof

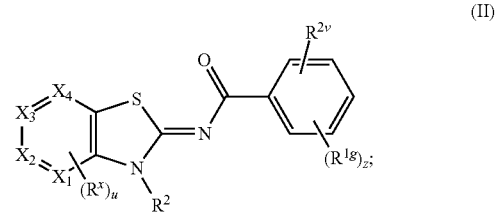

(II)

(2a) treating compounds of formula (II) or salts thereof with compounds of formula HO-$A^2$ or HO—$(CR^{1a}R^{1b})_{q1}$—O—$R^p$ wherein $R^p$ is hydrogen or a hydroxy-protecting group; or salts thereof, to produce compounds of formula (IIIa) or (IIIb) respectively, or salts thereof

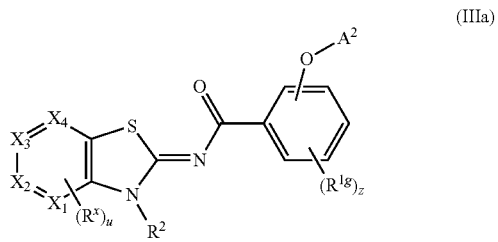

(IIIa)

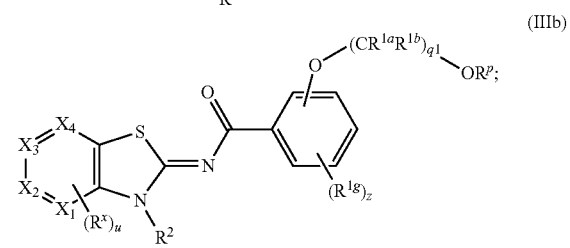

(IIIb)

and (2b) deprotect compounds of formula (IIIb) or salts thereof wherein $R^p$ is a hydroxy-protecting group to form the compound of formula (Ib) or salts thereof

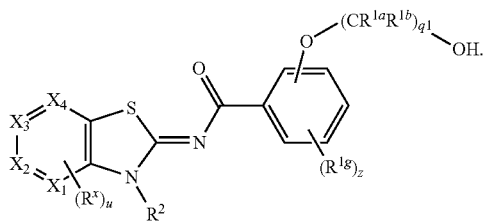
(Ib)

Also provided is a process for the preparation of compounds of formula (Ma) or salts thereof in which $X_1$, $X_2$, $X_3$, $X_4$, $R^2$, $R^x$, u, $A^2$, $R^{1g}$, and z are as disclosed in the Summary and Detailed Description sections; said process comprising (1a) treating compounds of formula (IV)

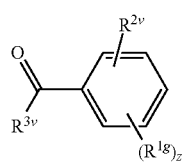
(IV)

wherein $R^{2v}$ is halogen or sulfonate; and $R^{3v}$ is halogen or OH; with a thiocyanate source to produce compounds of formula (V)

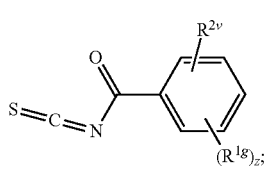
(V)

(1b) reacting compounds of formula (V) with compounds of formula (VI)

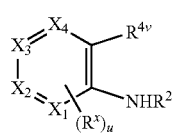
(VI)

wherein $R^{4v}$ is halogen or sulfonate to produce compounds of formula (II) or salts thereof

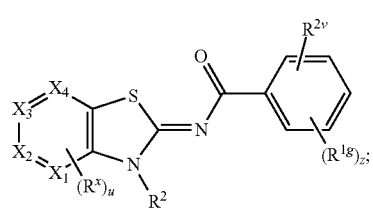
(II)

and (2a) treating compounds of formula (II) or salts thereof with compounds of formula $HO-A^2$ or salts thereof to produce compounds of formula (Ma) or salts thereof

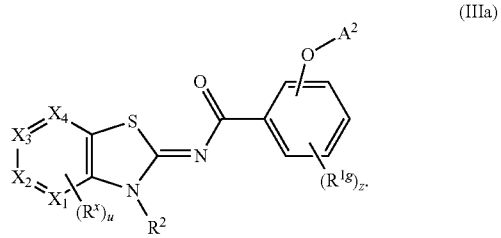
(IIIa)

Also included is a process for the preparation of compounds of formula (Ib) or salts thereof in which $X_1$, $X_2$, $X_3$, $X_4$, $R^2$, $R^x$, u, $R^{1g}$, $R^{1a}$, $R^{1b}$, q1, and z are as disclosed in the Summary and Detailed Description sections; said process comprising (1a) treating compounds of formula (IV)

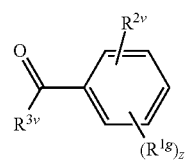
(IV)

wherein $R^{2v}$ is halogen or sulfonate; and $R^{3v}$ is halogen or OH; with a thiocyanate source to produce compounds of formula (V)

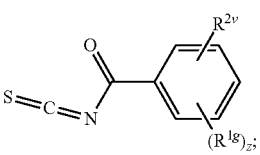
(V)

(1b) reacting compounds of formula (V) with compounds of formula (VI)

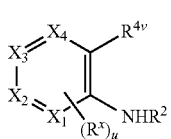
(VI)

wherein $R^{4v}$ is halogen or sulfonate to produce compounds of formula (II) or salts thereof

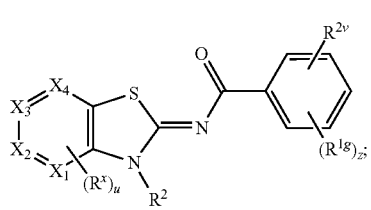
(II)

(2a) treating compounds of formula (II) or salts thereof with compounds of formula HO—$(CR^{1a}R^{1b})_{q1}$—O—$R^p$ wherein $R^p$ is hydrogen or a hydroxy-protecting group, or salts thereof, to produce compounds of formula (IIIb) or salts thereof

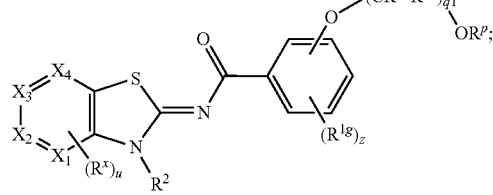
(IIIb)

and (2b) deprotect compounds of formula (IIIb) or salts thereof wherein $R^p$ is a hydroxy-protecting group to form the compound of formula (Ib) or salts thereof

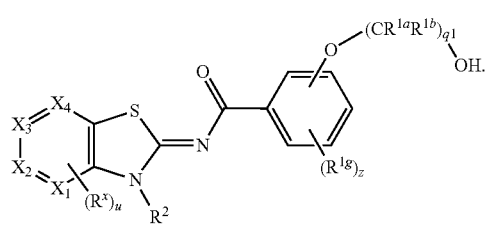
(Ib)

Contemplated too is a process for the preparation of compounds of formula (I-i) or salts thereof in which $X_1$, $X_2$, $X_3$, $X_4$, $R^2$, $R^x$, u, $R^{1g}$, $R^{1a}$, $R^{1b}$, q1, $A^2$, and z are as disclosed in the Summary and Detailed Description sections; said process comprising (1a) treating compounds of formula (IV-i)

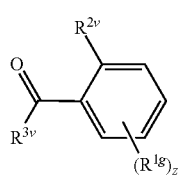
(IV-i)

wherein $R^{2v}$ is halogen or sulfonate; and $R^{3v}$ is halogen or OH; with a thiocyanate source to produce compounds of formula (V-i)

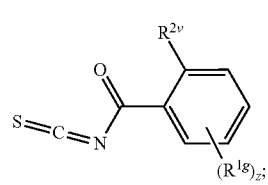
(V-i)

(1b) reacting compounds of formula (V-i) with compounds of formula (VI)

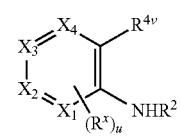
(VI)

wherein $R^{4v}$ is halogen or sulfonate to produce compounds of formula (II-i) or salts thereof

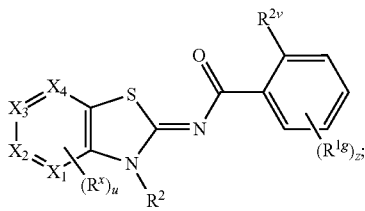
(II-i)

(2a) treating compounds of formula (II-i) or salts thereof with compounds of formula HO-$A^2$ or HO—$(CR^{1a}R^{1b})_{q1}$—O—$R^p$ wherein $R^p$ is hydrogen or a hydroxy-protecting group, or salts thereof, to produce compounds of formula (IIIa-i) or (IIIb-i) respectively, or salts thereof

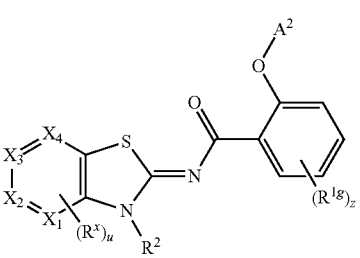
(IIIa-i)

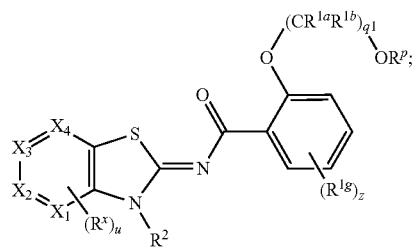
(IIIb-i)

and (2b) deprotect compounds of formula (IIIb-i) or salts thereof wherein $R^p$ is a hydroxy-protecting group to form the compound of formula (Ib-i) or salts thereof

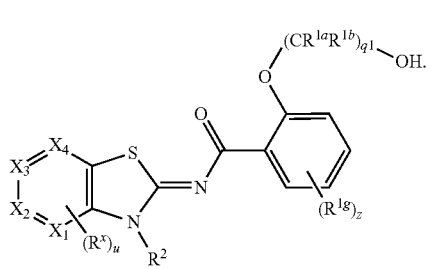 (Ib-i)

Also provided is a process for the preparation of compounds of formula (IIIa-i) or salts thereof in which $X_1$, $X_2$, $X_3$, $X_4$, $R^2$, $R^x$, u, $A^2$, $R^{1g}$, and z are as disclosed in the Summary and the Detailed Description sections; said process comprising (1a) treating compounds of formula (IV-i)

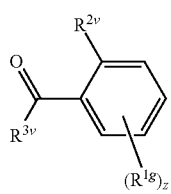 (IV-i)

wherein $R^{2v}$ is halogen or sulfonate; and $R^{3v}$ is halogen or OH; with a thiocyanate source to produce compounds of formula (V-i)

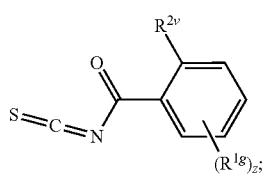 (V-i)

(1b) reacting compounds of formula (V-i) with compounds of formula (VI)

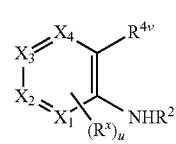 (VI)

wherein $R^{4v}$ is halogen or sulfonate to produce compounds of formula (II-i) or salts thereof

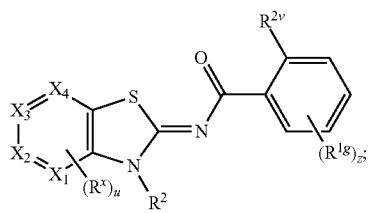 (II-i)

and (2a) treating compounds of formula (II-i) or salts thereof with compounds of formula HO-$A^2$ or salts thereof to produce compounds of formula (IIIa-i) or salts thereof

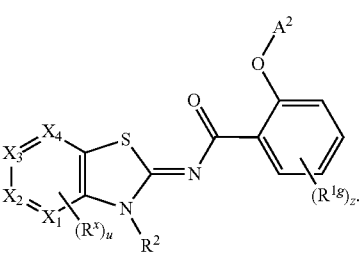 (IIIa-i)

Also included is a process for the preparation of compounds of formula (Ib-i) or salts thereof in which $X_1$, $X_2$, $X_3$, $X_4$, $R^2$, $R^x$, u, $R^{1g}$, $R^{1a}$, $R^{1b}$, q1, and z are as disclosed in the Summary and Detailed Description sections; said process comprising (1a) treating compounds of formula (IV-i)

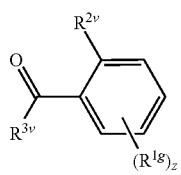 (IV-i)

wherein $R^{2v}$ is halogen or sulfonate; and $R^{3v}$ is halogen or OH; with a thiocyanate source to produce compounds of formula (V-i)

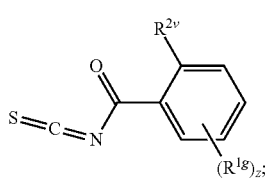 (V-i)

(1b) reacting compounds of formula (V-i) with compounds of formula (VI)

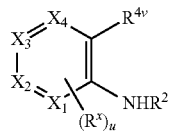

(VI)

wherein $R^{4v}$ is halogen or sulfonate to produce compounds of formula (II-i) or salts thereof

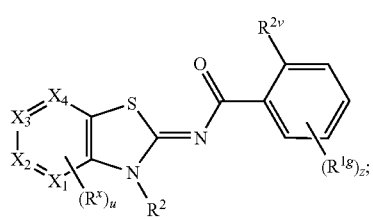

(II-i)

(2a) treating compounds of formula (II-i) or salts thereof with compounds of formula HO—$(CR^{1a}R^{1b})_{q1}$—O—$R^p$ wherein $R^p$ is hydrogen or a hydroxy-protecting group, or salts thereof, to produce compounds of formula (IIIb-i) or salts thereof

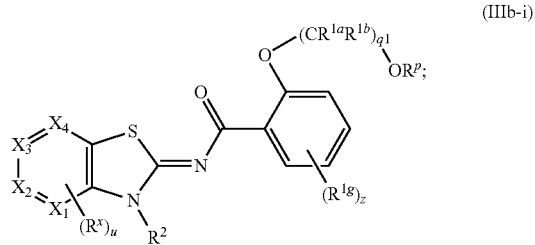

(IIIb-i)

and (2b) deprotect compounds of formula (IIIb-i) or salts thereof wherein $R^p$ is a hydroxy-protecting group to form the compound of formula (Ib-i) or salts thereof

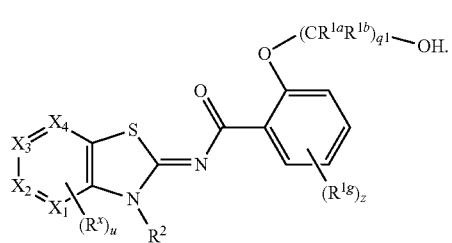

(Ib-i)

Another aspect relates to processes for the preparation of compounds of formula (I), (I-i), (IIIa), (IIIa-i), (Ib), or (Ib-i), or salts thereof, as described above wherein $X_1$, $X_2$, $X_3$, $X_4$, $R^x$, u, $R^{1g}$, $R^{1a}$, $R^{1b}$, q1, z, $A^1$, and $A^2$ are as described in the Summary, and $R^2$ is $C_2$-$C_{10}$ alkyl.

Another aspect relates to processes for the preparation of a group of compounds of formula (I), (I-i), (IIIa), (IIIa-i), (Ib), or (Ib-i), or salts thereof, as described above wherein $R^x$, u, $R^{1g}$, $R^{1a}$, $R^{1b}$, q1, z, $A^1$, and $A^2$ are as described in the Summary, $X_2$ is N, $X_1$, $X_3$, and $X_4$ are CH.

Yet another aspect relates to processes for the preparation of a group of compounds of formula (I), (I-i), (IIIa), (IIIa-i), (Ib), or (Ib-i), or salts thereof, as described above wherein $R^x$, u, $R^{1g}$, $R^{1a}$, $R^{1b}$, q1, z, $A^1$, and $A^2$ are as described in the Summary, $X_4$ is N, $X_1$, $X_2$, and $X_3$ are CH.

Yet another aspect relates to processes for the preparation of a group of compounds of formula (I), (I-i), (IIIa), (IIIa-i), (Ib), or (Ib-i), or salts thereof, as described above wherein $R^x$, u, $R^{1g}$, $R^{1a}$, $R^{1b}$, q1, z, $A^1$, and $A^2$ are as described in the Summary, $X_2$ is N, $X_1$, $X_3$, and $X_4$ are CH, and $R^2$ is $C_2$-$C_{10}$ alkyl.

Yet another aspect relates to processes for the preparation of a group of compounds of formula (I), (I-i), (IIIa), (IIIa-i), (Ib), or (Ib-i), or salts thereof, as described above wherein $R^x$, u, $R^{1g}$, $R^{1a}$, $R^{1b}$, q1, z, $A^1$, and $A^2$ are as described in the Summary, $X_4$ is N, $X_1$, $X_2$, and $X_3$ are CH, and $R^2$ is $C_2$-$C_{10}$ alkyl.

Yet another aspect relates to processes for the preparation a group of compounds of formula (I), (I-i), (Ib), or (Ib-i), or salts thereof, as described above wherein $X_1$, $X_2$, $X_3$, $X_4$, $R^2$, $R^x$, u, $R^{1g}$, $R^{1a}$, $R^{1b}$, q1, z, and $R^2$ are as described in the Summary, and $A^1$ is —$C(R^{1a}R^{1b})_{q1}$—OH. In one embodiment, the hydroxy group of —$(CR^{1a}R^{1b})_{q1}$—OH is a secondary or tertiary hydroxy. In another embodiment, the hydroxy group of —$(CR^{1a}R^{1b})_{q1}$—OH is a secondary or tertiary hydroxy; and $R^p$ in step (2a) is a hydroxy-protecting group. In yet another embodiment, the hydroxy group of —$(CR^{1a}R^{1b})_{q1}$—OH is a secondary hydroxy, and $R^p$ in step (2a) is a hydroxy-protecting group. In another embodiment, the hydroxy group of —$(CR^{1a}R^{1b})_{q1}$—OH is a tertiary hydroxy; and $R^p$ in step (2a) is hydrogen. Within these embodiments, an example of the hydroxy-protecting group includes, but not limited thereto, alkoxyalkyl (e.g methoxymethyl). $R^{1a}$, $R^{1b}$, and q1 are as described in the Summary and embodiments herein above.

Yet another aspect relates to processes for the preparation a group of compounds of formula (I), (I-i), (IIIa), or (IIIa-i), or salts thereof, as described above wherein $X_1$, $X_2$, $X_3$, $X_4$, $R^2$, $R^x$, u, $R^{1g}$, z, $A^1$, and $A^2$ are as described in the Summary, $A^1$ is $A^2$, and $A^2$ is $N(R^b)(R^c)$ wherein $R^b$ and $R^c$ are as described in the Summary. In one embodiment, $R^b$ and $R^c$ are the same or different, and are each independently hydrogen or alkyl. In another embodiment, $R^b$ is hydrogen and $R^c$ is alkyl. In yet another embodiment, $R^b$ is hydrogen and $R^c$ is tert-butyl.

Yet another aspect relates to processes for the preparation of a group of compounds of formula (I), (I-i), (IIIa), or (IIIa-i), or salts thereof, as described above wherein $X_1$, $X_2$, $X_3$, $X_4$, $R^2$, $R^x$, u, $R^{1g}$, z, $A^1$, and $A^2$ are as described in the Summary, $A^1$ is $A^2$, and $A^2$ is —$(CR^{1a}R^{1b})_q$-$G^{1c}$ wherein $R^{1a}$, $R^{1b}$, q, and $G^{1c}$ are as described in the Summary. In one embodiment, $R^{1a}$ and $R^{1b}$ are hydrogen, q is 1 or 2, and $G^{1c}$ is optionally substituted monocyclic heterocycle. In another embodiment, $R^{1a}$ and $R^{1b}$ are hydrogen, q is 1 or 2, and $G^{1c}$ is optionally substituted pyrrolidinyl.

Yet another aspect relates to processes for the preparation a group of compounds of formula (I), (I-i), (Ib), or (Ib-i), or salts thereof, as described above wherein $X_1$, $X_2$, $X_3$, $X_4$, $R^x$, u, $R^{1a}$, $R^{1b}$, $R^{1g}$, q1, and z are as described in the Summary, $R^2$ is $C_2$-$C_{10}$ alkyl and $A^1$ is —$C(R^{1a}R^{1b})_{q1}$—OH. In one embodiment, the hydroxy group of —$(CR^{1a}R^{1b})_{q1}$—OH is a secondary or tertiary hydroxy. In another embodiment, the hydroxy group of —$(CR^{1a}R^{1b})_{q1}$—OH is a secondary or tertiary hydroxy; and $R^p$ in step (2a) is a hydroxy-protecting group. In yet another embodiment, the hydroxy group of —(CR$^{1a}$R$^{1b}$)$_{q1}$—OH is a secondary hydroxy; and R$^p$ in step (2a) is a hydroxy-protecting group. In yet another embodiment, the hydroxy group of —(CR$^{1a}$R$^{1b}$)$_{q1}$—OH is a tertiary hydroxy; and R$^p$ in step (2a) is hydrogen. Within these embodiments, an example of the hydroxy-protecting group includes, but not limited thereto, alkoxyalkyl (e.g methoxymethyl). R$^{1a}$, R$^{1b}$, and q1 are as described in the Summary and embodiments herein above.

Yet another aspect relates to processes for the preparation a group of compounds of formula (I), (I-i), (IIIa), or (IIIa-i) or salts thereof as described above wherein X$_1$, X$_2$, X$_3$, X$_4$, R$^x$, u, R$^{1g}$, and z are as described in the Summary, R$^2$ is C$_2$-C$_{10}$ alkyl, A$^1$ is A$^2$, and A$^2$ is N(R$^b$)(R$^c$) wherein R$^b$ and R$^c$ are as described in the Summary. In one embodiment, R$^b$ and R$^c$ are the same or different, and are each independently hydrogen or alkyl. In another embodiment, R$^b$ is hydrogen and R$^c$ is alkyl. In yet another embodiment, R$^b$ is hydrogen and R$^c$ is tert-butyl.

Yet another aspect relates to processes for the preparation of a group of compounds of formula (I), (I-i), (IIIa), or (IIIa-i) or salts thereof as described above wherein X$_1$, X$_2$, X$_3$, X$_4$, R$^x$, u, R$^{1g}$, and z are as described in the Summary, R$^2$ is C$_2$-C$_{10}$ alkyl, A$^1$ is A$^2$, and A$^2$ is —(CR$^{1a}$R$^{1b}$)$_q$-G$^{1c}$ wherein R$^{1a}$, R$^{1b}$, q, and G$^{1c}$ are as described in the Summary. In one embodiment, R$^{1a}$ and R$^{1b}$ are hydrogen, q is 1 or 2, and G$^{1c}$ is optionally substituted monocyclic heterocycle. In another embodiment, R$^{1a}$ and R$^{1b}$ are hydrogen, q is 1 or 2, and G$^{1c}$ is optionally substituted pyrrolidinyl.

Within the last 6 aspects of the processes described above, one embodiment is directed to, for example, the preparation of a subgroup of compounds of formula (I), (I-i), (IIIa), (IIIa-i), (Ib), and (Ib-i), or salts thereof, wherein X$_2$ is N, X$_1$, X$_3$, and X$_4$ are CH. Another embodiment is directed to, for example, the preparation of a subgroup of compounds of formula (I), (I-i), (IIIa), (IIIa-i), (Ib), and (Ib-i) wherein X$_4$ is N, X$_1$, X$_2$, and X$_3$ are CH.

R$^{1g}$ and z for the groups and subgroups of compounds of formula of formula (I), (I-i), (IIIa), (IIIa-i), (Ib), and (Ib-i), or salts thereof, prepared using the processes described above have values as set forth in the Summary. For example, R$^{1g}$ is C$_1$-C$_4$ alkyl, C$_2$-C$_4$ alkenyl, C$_2$-C$_4$ alkynyl, halogen, C$_1$-C$_4$ haloalkyl, —CN, or —OR$^f$ wherein R$^f$ is as disclosed in the Summary, and z is 0, 1, or 2. In another embodiment, R$^{1g}$ is C$_1$-C$_4$ alkyl, C$_1$-C$_4$ haloalkyl, halogen, or —CN, and z is 0, 1, or 2. In yet another embodiment, R$^{1g}$ is C$_1$-C$_4$ alkyl, C$_1$-C$_4$ haloalkyl, or —CN, and z is 0 or 1. In yet another embodiment, R$^{1g}$ is C$_1$-C$_4$ haloalkyl and z is 1.

Another aspect relates to compounds of formula (I), (I-i), (IIIa), (IIIa-i), (Ib), or (Ib-i), or salts thereof, prepared using the processes as described above wherein the variables X$_1$, X$_2$, X$_3$, X$_4$, R$^2$, R$^x$, u, R$^{1a}$, R$^{1b}$, R$^{1g}$, q1, z, A$^1$, and A$^2$ are as described in the Summary and Detailed Description sections.

A further aspect relates to relates to compounds of formula (II) or (II-i), or salts thereof, prepared using the processes as described above wherein the variables X$_1$, X$_2$, X$_3$, X$_4$, R$^2$, R$^x$, u, R$^{2v}$, R$^{1g}$, and z are as described in the Summary and Detailed Description sections. In one embodiment, R$^{2v}$ is halogen. In another embodiment, R$^{2v}$ is F.

The processes described are exemplified in the following schemes 1-2 and specific examples. These schemes and specific examples are intended to illustrate processes of the invention and are not meant to limit the scope of the invention in any way.

Abbreviations used in the descriptions of the Schemes and the Examples that follow are: DMSO for dimethylsulfoxide, OTs for p-toluenesulfonate, OMs for methanesulfonate, and OTf for trifluoromethanesulfonate.

Scheme 1

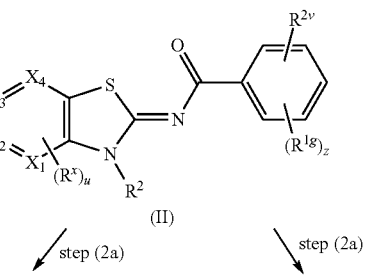

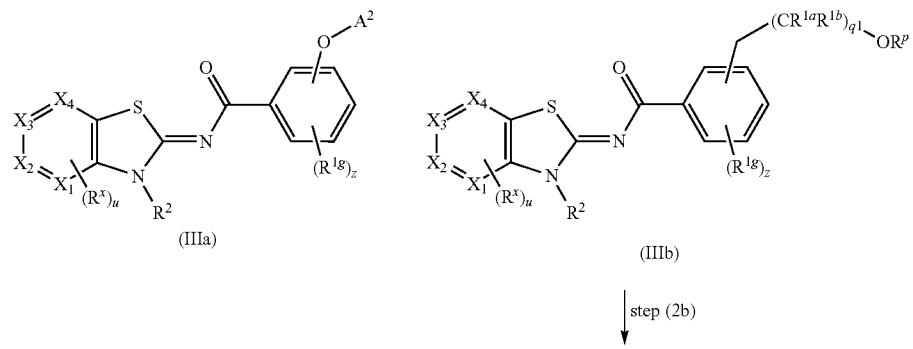

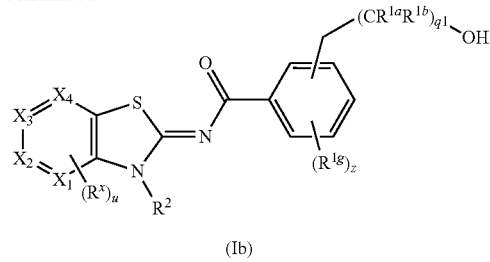

(Ib)

As shown in Scheme 1, compounds of formula (II) or salts thereof wherein $R^{2v}$ is halogen or sulfonate (e.g. OTf, or OMs), $X_1$, $X_2$, $X_3$, $X_4$, $R^2$, $R^x$, u, $R^{1g}$, and z are as described in the Summary and Detailed Description sections, is treated with compounds of formula HO-$A^2$ or HO—$(CR^{1a}R^{1b})_{q1}$—O—$R^p$ wherein $A^2$, $R^{1a}$, $R^{1b}$ and q1 are as described in the Summary and Detailed Description sections, and wherein $R^p$ is hydrogen or a hydroxy-protecting group, or salts thereof, to produce compounds of formula (IIIa) or (IIIb), or salts thereof, in step (2a).

Typically, HO-$A^2$ and HO$(CR^{1a}R^{1b})_{q1}$—O—$R^p$, or salts thereof, used in step (2a) are purchased from a commercial source or prepared using synthetic methods analogous to those known in the art. For example, HO$(CR^{1a}R^{1b})_{q1}$—O—$R^p$ wherein $R^p$ is hydrogen or a hydroxy-protecting group can be prepared from commercially available hydroxy substituted carboxylic esters. The secondary or the tertiary hydroxy group of the carboxylic esters can be left un-protected or selectively protected, followed by treatment with a reducing agent such as, but not limited to, lithium aluminum hydride to form the mono-protected or unprotected diols. Examples for more specific conditions for accomplishing the reduction reaction include treating the unprotected or protected hydroxy substituted carboxylic esters with lithium aluminum hydride in tetrahydrofuran, at about room temperature, for about 1 to about 36 hours.

The reaction of step (2a) is generally accomplished either in the presence of a strong organic or inorganic base or by a transition-metal catalyzed cross-coupling reaction in the presence of a suitable ligand. Examples of base include, but not limited to, n-butyl lithium, alkali metal alkoxides (e.g. sodium tert-butoxide, lithium methoxide), alkali metal hydrides (e.g. sodium hydride, potassium hydride), alkali metal hydroxides (e.g. sodium hydroxide, potassium hydroxide), 1,8-diazabicyclo[5.4.0]undec-7-ene (DBU), or carbonates such as potassium carbonates, cesium carbonate, or sodium carbonate. In one embodiment, the base is alkali metal alkoxide such as, but not limited to, sodium or potassium tert-butoxide. Preferably the amount of base present is at least about 1.5 molar equivalents relative to the amount of the compound of formula (II) or salts thereof present. More preferably, the amount is in the range of about 2 to about 3 molar equivalents relative to the amount of the compound of formula (II) or salts thereof present, or of about 1.75 to about 2.5 molar equivalents of the amount of the compound of formula (II) or salts thereof present.

A solution of a base in a first solvent is first treated with HO-$A^2$ or HO$(CR^{1a}R^{1b})_{q1}R^p$ wherein $A^2$, $R^{1a}$, $R^{1b}$, q1 and $R^p$ have meanings as described herein above, or salts thereof, at low temperature (preferably at a range from about 0° C. to about 5° C.) for about 30 minutes to about 1 hour before slow addition of a solution or slurry of compounds of formula (II) or salts thereof in a second solvent, resulting in a slurry that can be maintained by agitation such as stirring, shaking, or bubbling of an inert gas, such as nitrogen, through the solvent. Preferably the reaction is carried out under an inert atmosphere such as nitrogen, with stirring.

The reaction of step (2a) is carried out at a temperature within the range from about 0° C. to about the reflux temperature of the solvent employed, for example, from about 0° C. to about 80° C., or from about 0° C. to about 40° C., or at a temperature lower than room temperature, or from about 0° C. to about room temperature, or from about 0° C. to about 10° C., and more preferably from about 0° C. to about 5° C. Examples of suitable solvents that can be employed for the reaction of step (2a) include, but not limited to, tetrahydrofuran, acetonitrile, 1,4-dioxane, toluene, and N,N-dimethylformamide. The first solvent and the second solvent can be the same or different. Preferably the first and the second solvent are the same and is anhydrous tetrahydrofuran. The anhydrous tetrahydrofuran suitable for the reaction preferably contains less than about 1% of water by weight, preferably about 0.1% to about 1% of water by weight, and more preferably, containing less than or equal to about 0.1% of water by weight.

Typically HO-$A^2$ and HO$(CR^{1a}R^{1b})_{q1}$—O—$R^p$, or salts thereof, used are in excess of the compounds of formula (II) or salts thereof present, for example, at least about 2 molar equivalents relative to the amount of the compound of formula (II) or salts thereof present. More preferably, the amount is in the range of about 2 to about 3 molar equivalents relative to the amount of the compound of formula (II) or salts thereof present, or of about 2 molar equivalents of the amount of the compound of formula (II) or salts thereof present.

Preferably, the reaction is quenched and neutralized by the addition of an acid to the reaction mixture before isolation of the product. Examples of suitable acids include, but are not limited to, phosphoric acid, acetic acid, hydrochloric acid, and sulfuric acid. In one embodiment, the quenching step is conducted at a temperature from about 0° C. to about room temperature, for example, in the range from about 0° C. to about 10° C., or for example, in the range from about 0° C. to about 5° C. The amount of acid added is to maintain the pH of the mixture at neutral or slightly acidic, for example, to maintain a pH of about 4.

In one embodiment, the process of step (2a) comprises the slow addition of the HO-$A^2$ or HO$(CR^{1a}R^{1b})_{q1}$—O—$R^p$, or salts thereof, to a stirred solution/slurry of sodium or potassium tert-butoxide in anhydrous tetrahydrofurn at a temperature in the range of about 0° C. to about room temperature, for example, in the range of about 0° C. to about 10° C., or for example, in the range of about 0° C. to about 5° C. The reaction mixture is agitated for about 30 minutes to about 1 hour at the aforementioned temperatures. A solution/suspension of compounds of formula (II) or salts thereof in anhydrous tetrahydrofuran is then added to the reaction mixture at the aforementioned temperature. The resulting mixture is then stirred at a temperature in the range of about 0° C. to about room temperature, for example, in the range of about 0° C. to about 10° C., or in the range of about 0° C. to about 5° C., for a period of about 1 hour to about 10 hours. The reaction is then quenched by the addition of an acid at a temperature in the range of about 0° C. to about room temperature, for example, in the range of about 0° C. to about 10° C., or in the range of about 0° C. to about 5° C.

In accordance with the present invention, a process is provided for preparing compounds of formula (Ib) or (I) wherein $A^1$ is —$(CR^{1a}R^{1b})_{q1}$—OH, or salts thereof, from compounds of formula (IIIb) wherein $R^p$ is an hydroxy-protecting group as shown in step (2b). In one embodiment the hydroxy-protecting group is alkoxyalkyl such as, but not limited to, methoxymethyl.

In one embodiment, step (2b) is carried out by treating compounds of formula (IIIb) wherein $R^p$ is an hydroxy-protecting group with equimolar or excess acid including, but not limited to, hydrochloric acid, trifluoroacetic acid, acetic acid, and sulfuric acid, and in the presence of a suitable solvent such as, but not limited to, water, methanol, ethanol, isopropanol, or dichloromethane while maintaining the reaction temperature within the range from about room temperature to about 70° C., for example, from about room temperature to about 60° C., or at about 60° C., to form an acid salt of formula (Ib) or formula (I) wherein $A^1$ is —$(CR^{1a}R^{1b})_{q1}$—OH. The acid salt of formula (I) can be treated with about equimolar amount of sodium bicarbonate or other strong base to form the free base of formula (Ib) or formula (I) wherein $A^1$ is —$(CR^{1a}R^{1b})_{q1}$—OH.

Similarly, compounds of formula (I-i), formula (IIIa-i), formula (IIIb-i), or formula (Ib-i), or salts thereof, can be prepared from compounds of formula (II-i) using general procedures as described above.

and $X_1$, $X_2$, $X_3$, $X_4$, $R^2$, $R^x$, and u are as described in the Summary and Detailed Description sections, with compounds of formula (V) wherein $R^{2v}$ is halogen or sulfonate (e.g. OMs or OTf), and $R^{1g}$ and z are as described in the Summary and Detailed Description sections, employing the molar ratio of (VI):(V) within the range from about 1:1 to about 1:10, for example, from about 1:1 to about 1:5, or from about 1:1 to about 1:1.5. Typically the reaction is carried out in an appropriate solvent in which the reactants for the reaction can be dissolved. Suitable solvent can be polar or non-polar organic solvent that is inert to the reaction conditions. Examples of such solvents include, but are not limited to, chlorinated hydrocarbon such as chloroform, dichloromethane; acetone; ethyl acetate; acetonitrile; aromatic solvent such as toluene, xylene; tetrahydrofuran; dimethylsulfoxide; dimethylformamide; dimethylacetamide; dioxane; and methyl tert-butyl ether. In one embodiment, the solvent is anhydrous tetrahydrofuran. The reaction medium is preferably held at a temperature between about 0° C. to about 70° C., or between about 40° C. to about 70° C.

$R^{4v}$ and $R^{2v}$ can be the same or different, and are each selected from the group consisting of halogen or sulfonate (e.g. OTf or OMs). In one embodiment, $R^{2v}$ is halogen. In one embodiment, $R^{4v}$ is Cl or Br. In one embodiment, $R^{2v}$ is F.

Compounds of formula (V) can be prepared from the reaction of compounds of formula (IV) wherein $R^{3v}$ is halogen or OH, with a thiocynate source. Examples of a thiocyanate source include potassium thiocyante, sodium thiocyanate, and the like.

In one embodiment, $R^{3v}$ for compounds of formula (IV) is Cl, Br, F, or OH. In another embodiment $R^{3v}$ is Cl or Br. In yet another embodiment, $R^{3v}$ is OH.

The reaction is typically conducted in a suitable solvent such as those described for the transformation of (VI) to (II). In one embodiment, the solvent used is tetrahydrofuran.

Scheme 2

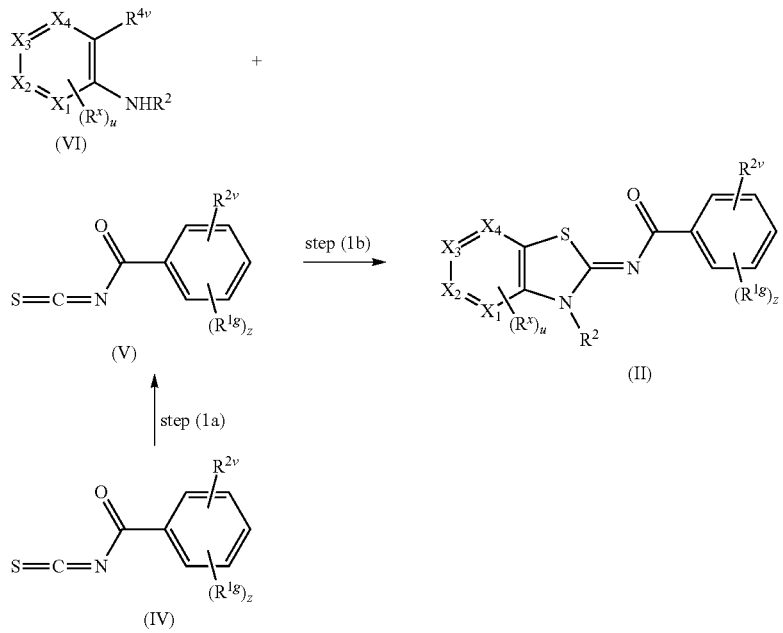

As shown in Scheme 2, the compounds of formula (II) or salt thereof is produced by treating compounds of formula (VI) wherein $R^{4v}$ is halogen, or sulfonate (e.g. OMs or OTf), Typically, the reaction is conducted by employing about equimolar of compounds of formula (IV) and the thiocyanate source, optionally in the presence of a base, and at a temperature ranging from about room temperature to about the refluxed temperature of the solvent employed, for example, from about room temperature to about 60° C., or from about 40° C. to about 50° C., or at about room temperature. The resulting compound is generally used in the next step without isolation. In some instances, the solvent can be removed under vacuo and the residue is used without further purification.

In one embodiment of the method of the invention, $R^{3v}$ is OH. Within this embodiment, the reaction is carried out by reacting about equimolar mixture of the compounds in the presence of a coupling reagent, a base, and optionally in the presence of a coupling auxiliary, at a temperature ranging from about 0° C. to about 70° C., for example, from about room temperature to about 50° C., or at about room temperature. Examples of coupling reagents include, but are not limited to, bis(2-oxo-3-oxazolidinyl)phosphinic chloride (BOPCl), 1,3-dicyclohexylcarbodiimide (DCC), polymer supported 1,3-dicyclohexylcarbodiimide (PS-DCC), O-(7-azabenzotriazol-1-yl)-N,N,N',N'-tetramethyluronium hexafluorophosphate (HATU), O-benzotriazol-1-yl-N,N,N',N'-tetramethyluronium tetrafluoroborate (TBTU), and 1-propanephosphonic acid cyclic anhydride. Non-limiting examples of coupling auxiliary include 1-hydroxy-7-azabenzotriazole (HOAT) and 1-hydroxybenzotriazole hydrate (HOBT).

Suitable examples of bases for reactions of compound (IV) wherein $R^{3v}$ is Cl, Br, or OH, include, but are not limited to, N-methyl morpholine, pyridine, N,N-dimethylaminopyridine, trimethylamine, triisopropylamine, diisopropylethylamine, and the like.

The compounds of formula (VI) can be obtained from a commercial vendor, for example, or can be prepared from reductive amination or alkylation of a suitable substituted heteroaryl amine using reaction conditions that are known in one skilled in the art.

Compounds of formula (II-i) wherein $X_1$, $X_2$, $X_3$, $X_4$, $R^x$, u, $R^2$, $R^{2v}$, $R^{1g}$, and z are as described in the Summary and Detailed Description sections, or salts thereof, can be prepared from the corresponding regioisomer of compounds (IV) using the procedures as detailed in Scheme 2.

Physiologically acceptable salts of compounds disclosed herein are within the scope of the invention. Examples of suitable salts include those derived from organic and inorganic acids such as, without limitation, hydrochloric acid, hydrobromic acid, phosphoric acid, sulfuric acid, methanesulfonic acid, acetic acid, tartaric acid, trifluoroacetic acid, lactic acid, sulfuric acid, benzenesulfonic acid, citric acid, maleic acid, fumaric acid, sorbic acid, salicylic acid, phthalic acid, and the like.

It can be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step can vary depending on the particular reactants employed and substituents present in the reactants used.

Unless otherwise specified, solvents, temperatures and other reaction conditions can be readily selected by one of ordinary skill in the art. Specific procedures are provided in the Examples section. Compounds and intermediates in the processes described can be worked up in the conventional manner, e.g. by eliminating the solvent from the residue and/or further purified according to methodologies generally known in the art such as, but not limited to, crystallization, distillation at various pressures, extraction, trituration, thin-layer chromatography, re-crystallization at high or low temperatures, and chromatography on solid supports such as silica gel, alumina. Unless otherwise described, the starting materials and reagents are either commercially available or can be prepared by one skilled in the art from commercially available materials using methods described in the chemical literature.

Various changes and modifications to the disclosed embodiments, including appropriate manipulation of the reaction conditions, reagents and sequence of the synthetic route, protection of any chemical functionality that can not be compatible with the reaction conditions, and deprotection at a suitable point in the reaction sequence of the method, are within the purview of the invention and can be made without departing from the spirit and scope thereof. Suitable protecting groups and the methods for protecting and deprotecting different substituents using such suitable protecting groups are well known to those skilled in the art; examples of which can be found in T. Greene and P. Wuts, Protecting Groups in Chemical Synthesis ($3^{rd}$ ed.), John Wiley & Sons, NY (1999), which is incorporated herein by reference in its entirety. Synthesis of the compounds of the invention can be accomplished by methods analogous to those described in the synthetic schemes described hereinabove and in specific examples.

Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it can be obtained by carrying out one of the above procedures using a pure geometric isomer as a starting material, or by resolution of a mixture of the geometric isomers of the compound or intermediates using a standard procedure such as re-crystallization or chromatographic separation.

EXAMPLES

The invention is illustrated by the following Examples which are given by way of example only.

Example 1

N-[(2Z)-3-butyl[1,3]thiazolo[4,5-c]pyridin-2(3H)-ylidene]-2-{[(2R)-2-hydroxypropyl]oxy}-5-(trifluoromethyl)benzamide Part A: Preparation of N-[(2Z)-3-butyl[1,3]thiazolo[4,5-c]pyridin-2(3H)-ylidene]-2-fluoro-5-(trifluoromethyl)benzamide Hydrochloride salt

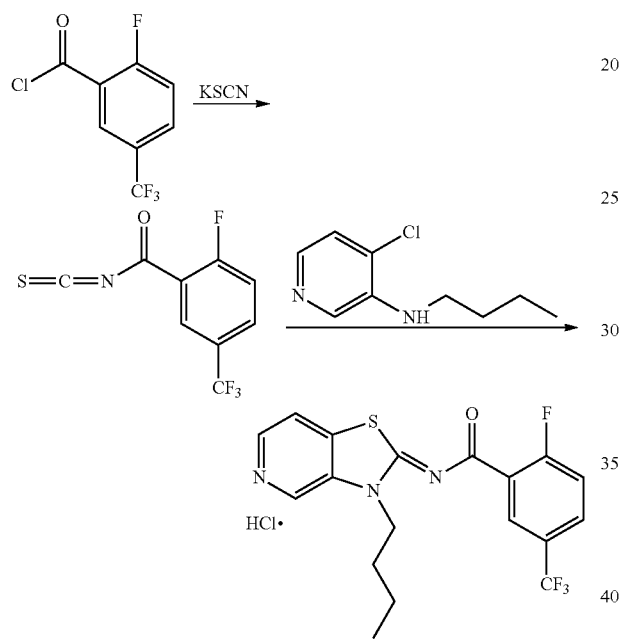

To a three-necked flask were charged potassium thiocyanate (200.0 g, 2.03 mol), and tetrahydrofuran (6.78 L). 2-Fluoro-5-(trifluoromethyl)benzoyl chloride (471.0 g, 2.07 mol) was added into the flask slowly at room temperature. The reaction mixture was stirred at room temperature for 5 hours or until less than 1% of the acid chloride remains. The reaction mixture was filtered to remove potassium chloride by-product, and rinsed with tetrahydrofuran (about 0.5 L). The combined solution of 2-fluoro-5-(trifluoromethyl)benzoyl isothiocyanate was charged back to the three-necked flask, followed by addition of N-butyl-4-chloropyridin-3-amine (266.0 g, 1.44 mol). The reaction mixture was heated to approximately 50° C., and stirred vigorously overnight or until less than 1% of N-butyl-4-chloropyridin-3-amine remains. The product suspension was then cooled to room temperature, and the product collected by filtration. The wet cake was washed with tetrahydrofuran (1.0 L), and dried under vacuum at 60° C. to give the desired product (584.0 g, 93% isolated yield). MS-ESI: 398 (M+1); $^1$H-NMR (CDCl$_3$-DMSO-d$_6$) δ 0.96 (3H, t, J=7.4 Hz), 1.45 (2H, m), 1.84 (2H, m), 4.58 (2H, d, J=7.6 Hz), 7.49 (1H, t, J=9.0 Hz), 7.92 (1H, m), 8.42 (1H, d, J=5.8 Hz), 8.46 (1H, dd, J=6.6, 2.5 Hz), 8.65 (1H, d, J=6.6 Hz), 9.37 (1H, s); $^{13}$-NMR (CDCl$_3$-DMSO-d$_6$) δ 13.50, 19.47, 29.12, 46.08, 118.07 (d, J=23 Hz), 119.70, 122.90 (q, J=269 Hz, CF$_3$), 123.96 (d, J=10 Hz), 124.84 (q, J=33 Hz, C—CF$_3$), 128.21, 128.78, 130.70, 134.50, 137.03, 141.20, 162.78 (d, J=262 Hz, C—F), 165.79, 170.06 (d, J=4.0 Hz).

Part B: Preparation of N-[(2Z)-3-butyl[1,3]thiazolo[4,5-c]pyridin-2(3H)-ylidene]-2-fluoro-5-(trifluoromethyl)benzamide

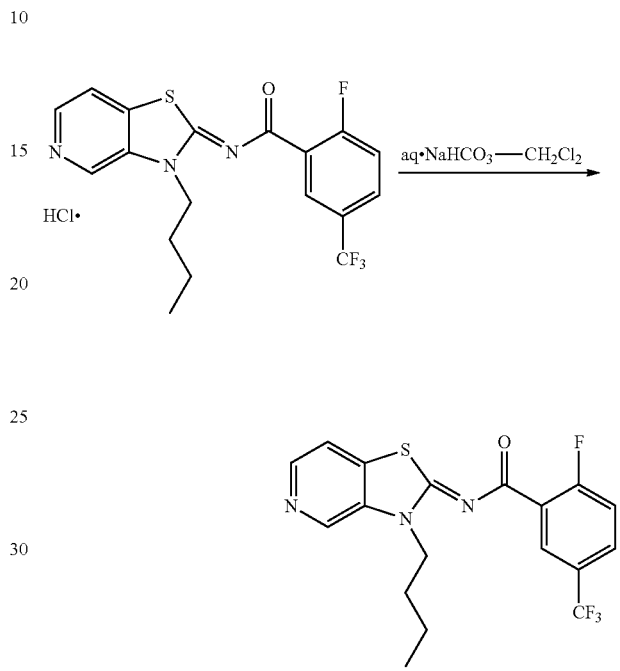

195.5 g of the hydrochloride salt (0.45 mol) from Part A of Example 1, and dichloromethane (3.2 L) were charged to a 5 L three-necked flask. 1.00 L of 5% sodium bicarbonate aqueous solution was added into the flask, and the biphasic mixture stirred at room temperature for 1 hour. The organic phase was separated and washed with 25% brine solution (0.80 L). The organic phase was concentrated under vacuum to 175.0 g (98%) of the freebase as a white solid. $^1$H-NMR (CDCl$_3$) δ 1.04 (3H, t, J=7.4 Hz), 1.51 (2H, m), 1.93 (2H, m), 4.56 (2H, t, J=7.4 Hz), 7.27 (1H, t, J=8.8 Hz), 7.69 (1H, d, J=5.3 Hz), 7.75 (1H, m), 8.52 (1H, d, J=5.3 Hz), 8.55 (1H, dd, J=6.7, 2.3 Hz), 8.75 (1H, s).

Part C: Preparation of N-[(2Z)-3-butyl[1,3]thiazolo[4,5-c]pyridin-2(3H)-ylidene]-2-{[(2R)-2-(methoxymethoxy)propyl]oxy}-5-(trifluoromethyl)benzamide

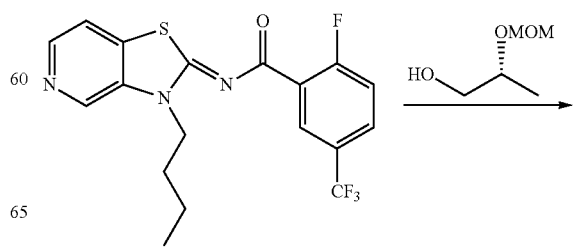

31

-continued

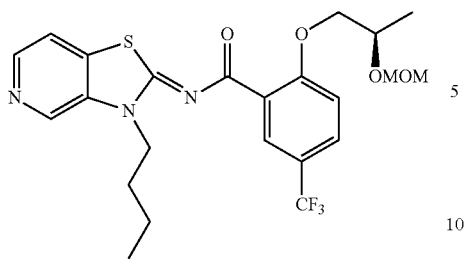

To a 250 mL three-necked flask were charged sodium tert-butoxide (97%, 0.69 g, 7.0 mmol), and anhydrous tetrahydrofuran (17 mL). The mixture was stirred, and cooled down to about 0° C. A solution of (R)-2-(methoxymethoxy)propan-1-ol (0.96 g, 8.0 mmol) in tetrahydrofuran (2.0 mL) was added slowly at the internal temperature <5° C. The solution was mixed at <5° C. for 30 minutes, followed by addition of the N-[(2Z)-3-butyl[1,3]thiazolo[4,5-c]pyridin-2(3H)-ylidene]-2-fluoro-5-(trifluoromethyl)benzamide (1.59 g, 4.0 mmol) from Part B of Example 1 in tetrahydrofuran (36 mL) at <0° C. The resulting mixture was stirred at about 0° C. for 4 hours or until less than 5% of starting material remains. 125 g of 1.5% $H_3PO_4$ aqueous solution was added slowly to the reaction mixture at <5° C. The resulting slurry was mixed at about 0° C. for 1 hour, and then allowed to warm up to room temperature. The slurry was stirred at room temperature for 5 hours, and the product collected by filtration. The wet cake was washed with water-acetonitrile (2:1) (20 mL), and dried under vacuum at 50° C. overnight with a slow flow of nitrogen to give a white solid (1.46 g, 73%). MS-ESI: 498 (M+1); $^1$H-NMR (DMSO-$d_6$) δ 0.94 (3H, t, J=7.4 Hz), 1.24 (3H, d, J=5.9 Hz), 1.41 (2H, m), 1.81 (2H, m), 3.23 (3H, s), 4.08 (3H, m), 4.52 (2H, t, J=7.5 Hz), 4.60 (1H, d, J=6.6 Hz), 4.75 (1H, d, J=6.9 Hz), 7.28 (1H, d, J=8.8 Hz), 7.75 (1H, d, J=8.8 Hz), 7.94 (1H, d, J=5.2 Hz), 8.24 (1H, d, J=2.2 Hz), 8.44 (1H, d, J=5.2 Hz), 8.95 (1H, s). $^{13}$C-NMR (CDCl$_3$-DMSO-$d_6$) δ 13.51, 17.28, 19.51, 29.28, 45.17, 54.50, 70.16, 72.23, 94.42, 113.39, 117.32, 120.10 (q, J=33 Hz, C—CF$_3$), 123.66 (q, J=268 Hz, CF$_3$), 126.05, 127.62, 128.75, 132.90, 133.14, 134.36, 142.71, 159.70, 164.56, 172.26.

Part D: Preparation of N-[(2Z)-3-butyl[1,3]thiazolo[4,5-c]pyridin-2(3H)-ylidene]-2-{[(2R)-2-hydroxypropyl]oxy}-5-(trifluoromethyl)benzamide

32

-continued

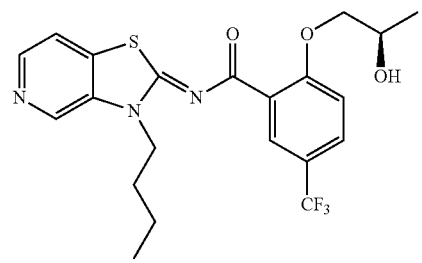

To a 250 mL three-necked flask were charged the product (1.40 g, 2.8 mmol) from Part C of Example 1 and isopropanol (45 mL). The slurry was heated to about 60° C., and concentrated hydrochloric acid solution (8.5 g) added slowly. The resulting mixture was stirred at 60° C. for 12 hours or until less than 3% of the starting material remains as determined by HPLC. The suspension was cooled to room temperature, and the product filtered to afford the title compound as a hydrochloride salt. The hydrochloride salt, isopropanol (14 mL) and water (7 ml) were charged into a 100 mL flask. The slurry was heated to about 75° C. to dissolve all of the solids, and 5% NaHCO$_3$ aqueous solution (9.4 g) was added slowly. The resulting mixture was stirred at about 75° C. for 15 minutes, and cooled down to about 30° C. over 4 hours. The product was collected by filtration and dried under vacuum at 50° C. overnight with a slow flow of nitrogen to give a white solid (1.00 g, 78%). MS-ESI: 454 (M+1); $^1$H-NMR (DMSO-$d_6$) δ 0.93 (3H, t, J=7.5 Hz), 1.19 (3H, d, J=5.8 Hz), 1.40 (2H, m), 1.81 (2H, m), 4.00 (3H, m), 4.52 (2H, t, J=7.5 Hz), 4.88 (1H, s), 7.34 (1H, d, J=8.6 Hz), 7.81 (1H, dd, J=8.6, 2.2 Hz), 7.99 (1H, d, J=5.2 Hz), 8.24 (1H, d, J=2.2 Hz), 8.48 (1H, d, J=5.2 Hz), 9.01 (1H, s); $^{13}$C-NMR (DMSO-$d_6$) δ, 13.55, 19.50, 20.04, 29.27, 45.23, 64.34, 74.12, 114.34, 117.46, 119.98 (q, J=32 Hz, C—CF$_3$), 123.77 (q, J=268 Hz, CF$_3$), 126.17, 127.64, 128.99, 132.99, 133.42, 134,31, 142.84, 160.12, 164.12, 172.41.

Example 2

N-[(2Z)-3-butyl[1,3]thiazolo[4,5-c]pyridin-2(3H)-ylidene]-2-{[(2S)-2-hydroxypropyl]oxy}-5-(trifluoromethyl)benzamide Part A: N-[(2Z)-3-butyl[1,3]thiazolo[4,5-c]pyridin-2(3H)-ylidene]-2-{[(2S)-2-(methoxymethoxy)propyl]oxy}-5-(trifluoromethyl)benzamide

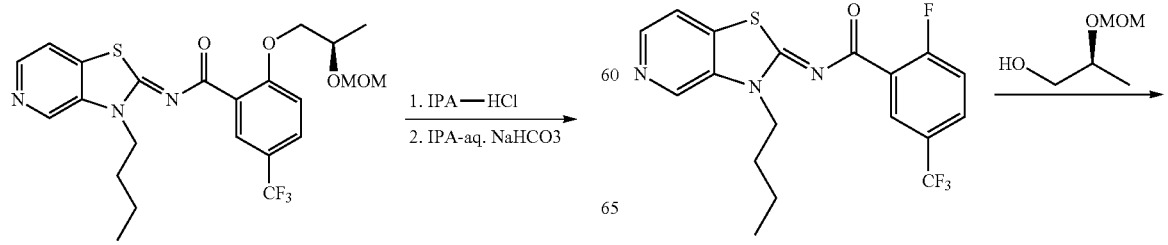

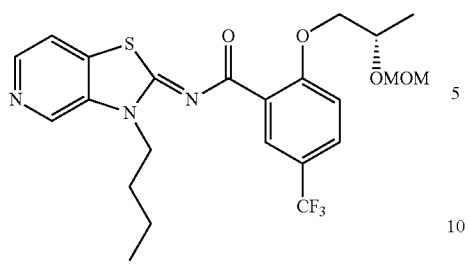

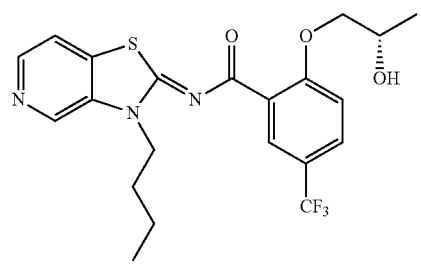

To a 250 mL three-necked flask were charged sodium tert-butoxide (97%, 0.69 g, 7.0 mmol), and anhydrous tetrahydrofuran (17 mL). The mixture was stirred, and cooled down to about 0° C. A solution of (S)-2-(methoxymethoxy) propan-1-ol (0.96 g, 8.0 mmol) in THF (2.0 mL) was added slowly at the internal temperature <5° C. The solution was mixed at <5° C. for 30 min., followed by addition of the product (1.59 g, 4.0 mmol) from Part B of Example 1 in anhydrous tetrahydrofuran (36 mL) at <0° C. The resulting mixture was stirred at about 0° C. for 4 hours or until less than 5% of starting material remains. 125 g of 1.5% $H_3PO_4$ aqueous solution was added slowly to the reaction mixture at <5° C. The resulting slurry was mixed at about 0° C. for 1 hour, and then allowed to warm up to room temperature. The slurry was stirred at room temperature for 5 hrs, and the product collected by filtration. The wet cake was washed with water-acetonitrile (2:1) (20 mL), and dried under vacuum at 50° C. overnight with a slow flow of nitrogen to give a white solid (1.48 g, 74%). MS-ESI: 498 (M+1); $^1$H-NMR (DMSO-$d_6$) δ 0.94 (3H, t, J=7.4 Hz), 1.24 (3H, d, J=5.9 Hz), 1.41 (2H, m), 1.81 (2H, m), 3.23 (3H, s), 4.08 (3H, m), 4.52 (2H, t, J=7.5 Hz), 4.60 (1H, d, J=6.6 Hz), 4.75 (1H, d, J=6.9 Hz), 7.28 (1H, d, J=8.8 Hz), 7.75 (1H, d, J=8.8 Hz), 7.94 (1H, d, J=5.2 Hz), 8.24 (1H, d, J=2.2 Hz), 8.44 (1H, d, J=5.2 Hz), 8.95 (1H, s). $^{13}$C-NMR (DMSO-$d_6$) δ 13.51, 17.28, 19.51, 29.28, 45.17, 54.50, 70.16, 72.23, 94.42, 113.39, 117.32, 120.10 (q, J=33 Hz, C—$CF_3$), 123.66 (q, J=268 Hz, $CF_3$), 126.05, 127.62, 128.75, 132.90, 133.14, 134.36, 142.71, 159.70, 164.56, 172.26.

Part B: Preparation of N-[(2Z)-3-butyl[1,3]thiazolo[4,5-c]pyridin-2(3H)-ylidene]-2-{[(2S)-2-hydroxypropyl]oxy}-5-(trifluoromethyl)benzamide To a 250 mL three-necked flask were charged the product (1.40 g, 2.8 mmol) from Part A of Example 2 and isopropanol (45 mL). The slurry was heated to about 60° C., and concentrated hydrochloric acid solution (8.5 g) added slowly. The resulting mixture was stirred at 60° C. for 12 hours or until less than 3% of the starting material remains by HPLC. The suspension was cooled down to room temperature, and the product filtered to afford the desired product as a hydrochloride salt. The hydrochloride salt, isopropanol (14 mL) and water (7 ml) were charged into a 100 mL flask. The slurry was heated to about 75° C. to dissolve all of the solids, and 5% NaHCO3 aqueous solution (9.4 g) added slowly. The resulting mixture was stirred at about 75° C. for 15 minutes, and cooled down to about 30° C. over 4 hours. The product was collected by filtration and dried under vacuum at 50° C. overnight with a slow flow of nitrogen to give a white solid (0.99 g, 78%). MS-ESI: 454 (M+1); $^1$H-NMR (DMSO-$d_6$) δ 0.93 (3H, t, J=7.5 Hz), 1.19 (3H, d, J=5.8 Hz), 1.40 (2H, m), 1.81 (2H, m), 4.00 (3H, m), 4.52 (2H, t, J=7.5 Hz), 4.88 (1H, s), 7.34 (1H, d, J=8.6 Hz), 7.81 (1H, dd, J=8.6, 2.2 Hz), 7.99 (1H, d, J=5.2 Hz), 8.24 (1H, d, J=2.2 Hz), 8.48 (1H, d, J=5.2 Hz), 9.01 (1H, s); $^{13}$C-NMR (DMSO-$d_6$) δ, 13.55, 19.50, 20.04, 29.27, 45.23, 64.34, 74.12, 114.34, 117.46, 119.98 (q, J=32 Hz, C—$CF_3$), 123.77 (q, J=268 Hz, $CF_3$), 126.17, 127.64, 128.99, 132.99, 133.42, 134,31, 142.84, 160.12, 164.12, 172.41.

Example 3

Preparation of N-[(2Z)-3-butyl[1,3]thiazolo[4,5-c]pyridin-2(3H)-ylidene]-2-(2-hydroxy-2-methylpropoxy)-5-(trifluoromethyl)benzamide

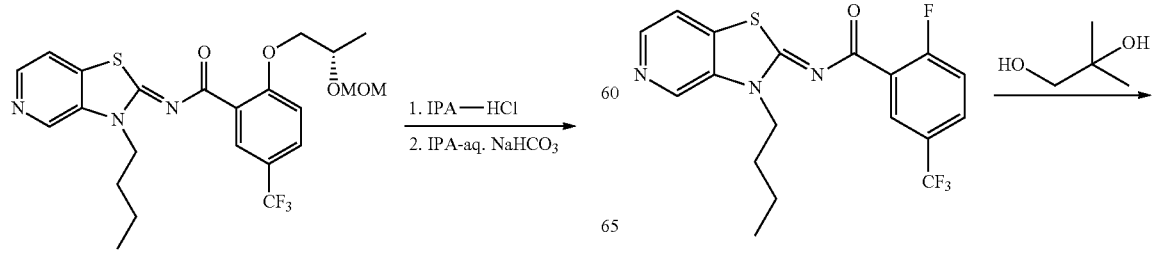

-continued

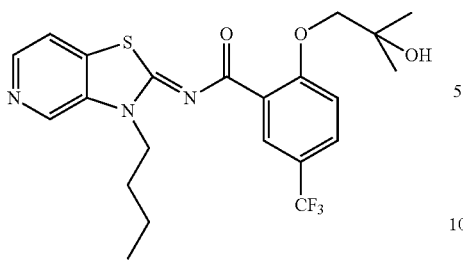

To a 250 mL three-necked flask were charged sodium tert-butoxide (97%, 0.99 g, 10 mmol), and anhydrous tetrahydrofuran (18 mL). The mixture was stirred, and cooled down to about 0° C. A solution of 2-methylpropane-1,2-diol (1.08 g, 12 mmol) in anhydrous tetrahydrofuran (2.0 mL) was added slowly at the internal temperature <5° C. The solution was mixed at <5° C. for 30 minutes, followed by addition of the product (1.59 g, 4.0 mmol) from Part B of Example 1 in anhydrous tetrahydrofuran (36 mL) at <0° C. The resulting mixture was stirred at about 0° C. for 4 hours or until less than 5% of starting material remains. 125 g of 1.5% $H_3PO_4$ aqueous solution was added slowly to the reaction mixture at <5° C. The resulting slurry was mixed at about 0° C. for 1 hour, and then allowed to warm up to room temperature. The slurry was stirred at room temperature for 5 hours, and the product collected by filtration. The wet cake was washed with water-acetonitrile (2:1) (20 mL), and dried under vacuum at 50° C. overnight with a slow flow of nitrogen to give a white solid (1.15 g, 62%). MS-ESI: 468 (M+1); $^1$H-NMR ($CDCl_3$-DMSO-$d_6$) δ 0.94 (3H, t, J=7.4 Hz). 1.25 (6H, s), 1.42 (2H, m), 1.84 (2H, m), 3.90 (2H, s), 4.48 (2H, t, J=7.4 Hz), 7.08 (1H, d, J=8.7 Hz), 7.62 (1H, dd, J=8.7, 2.3 Hz), 7.70 (1H, d, J=5.3 Hz), 8.32 (1H, d, J=2.3 Hz), 8.39 (1H, d, J=5.3 Hz), 8.73 (1H, s); $^{13}$C-NMR ($CDCl_3$-DMSO-$d_6$) δ 13.28, 19.53, 25.92, 29.20, 45.20, 68.79, 77.69, 114.07, 116.74, 120.98 (q, J=33 Hz, C—$CF_3$), 123.21 (q, J=268 Hz, $CF_3$), 125.51, 128.12, 128.65, 132.26, 132.64, 134.74, 142.49, 160.56, 164.58, 172.49.

Example 4

Preparation of N-[(2Z)-3-butyl[1,3]thiazolo[4,5-c]pyridin-2(3H)-ylidene]-2-(3-hydroxy-3-methylbutoxy)-5-(trifluoromethyl)benzamide

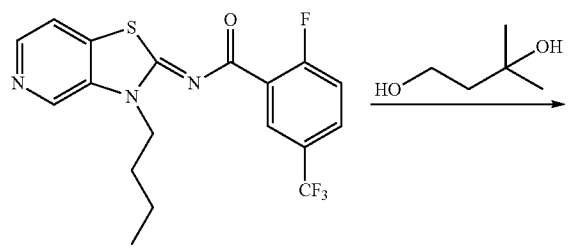

-continued

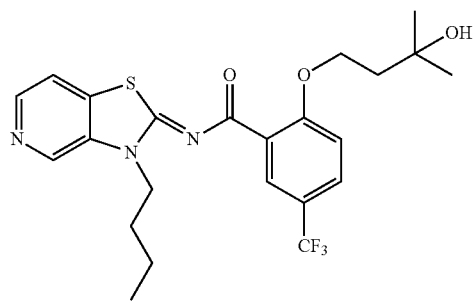

To a 250 mL three-necked flask were charged sodium tert-butoxide (97%, 0.99 g, 10 mmol), and anhydrous tetrahydrofuran (18 mL). The mixture was stirred, and cooled down to about 0° C. A solution of 3-methylbutane-1,3-diol (1.25 g, 12 mmol) in anhydrous tetrahydrofuran (2.0 mL) was added slowly at the internal temperature <5° C. The solution was mixed at <5° C. for 30 minutes, followed by addition of the product (1.59 g, 4.0 mmol) from Part B of Example 1 in anhydrous tetrahydrofuran (36 mL) at <0° C. The resulting mixture was stirred at about 0° C. for 4 hours or until less than 5% of starting material remains. 125 g of 1.5% $H_3PO_4$ aqueous solution was added slowly to the reaction mixture at <5° C. The resulting slurry was mixed at about 0° C. for 1 hour, and then allowed to warm up to room temperature. The slurry was stirred at room temperature for 5 hours, and the product collected by filtration. The wet cake was washed with water-acetonitrile (2:1) (20 mL), and dried under vacuum at 50° C. overnight with a slow flow of nitrogen to give a white solid (1.38 g, 72%). ESI-MS: 482 (M+1); $^1$H-NMR ($CDCl_3$-DMSO-$d_6$) δ 0.95 (3H, t, J=7.3 Hz). 1.18 (6H, s), 1.43 (2H, m), 1.83 (2H, m), 1.94 (2H, t, J=6.5 Hz), 4.26 (2H, t, J=6.5 Hz), 4.51 (2H, t, J=7.3 Hz), 7.24 (1H, d, J=8.6 Hz), 7.71 (1H, dd, J=8.7, 2.2 Hz), 7.84 (1H, d, J=5.2 Hz), 8.32 (1H, d, J=2.1 Hz), 8.40 (1H, d, J=5.2 Hz), 8.87 (1H, s); $^{13}$C-NMR ($CDCl_3$-DMSO-$d_6$) δ 13.44, 19.52, 29.26, 29.40, 41.16, 45.19, 65.65, 67.90, 112.76, 117.03, 120.11 (q, J=33 Hz, C—$CF_3$), 123.49 (q, J=269 Hz, $CF_3$), 125.11, 128.03, 128.87, 132.77, 132.82, 134.47, 142.58, 159.93, 164.52, 172.28.

Example 5

Preparation of 2-[(tert-butylamino)oxy]-N-[2Z)-3-butyl[1,3]thiazolo[4,5-c]pyridin-2(3H)-ylidene]-5-(trifluoromethyl)benzamide

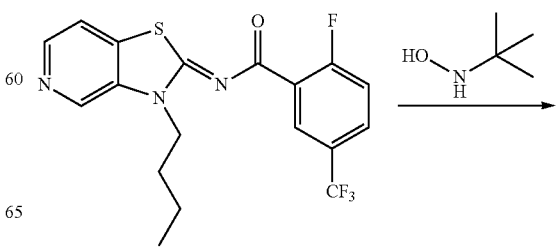

37
-continued

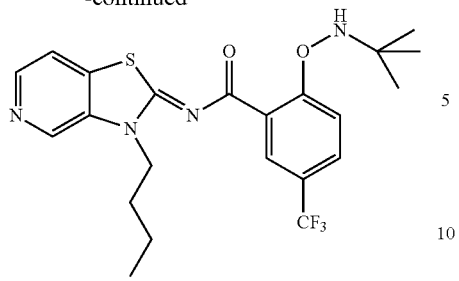

Tert-butylhydroxyamine HCl salt (1.51 g, 12.0 mmol) and anhydrous tetrahydrofuran (20 mL) were charged to a 100 mL round bottom flask. The thin slurry was cooled to 5° C., and triethylamine (1.27 g, 12.5 mmol) added. The pasty slurry was allowed to rise to room temperature and mixed at room temperature for 30 min. The TEA HCl salt was filtered off, and rinse with anhydrous tetrahydrofuran (5 mL). The filtrate was cooled to about 0° C. and sodium tert-butoxide (97%, 0.99 g, 10 mmol) added all at once. The mixture was stirred for 30 minutes and the product (1.59 g, 4.0 mmol) from Part B of Example 1 in tetrahydrofuran (36 mL) at <0° C. The resulting mixture was stirred at about 0° C. for 1 hour, and allowed to warm up to room temperature. The reaction mixture was stirred at room temperature overnight. The mixture was cooled to 0° C., and 125 g of 2% $H_3PO_4$ aqueous solution was added slowly to the reaction mixture at <5° C. The resulting slurry was mixed at about 0° C. for 1 hour, and then allowed to warm up to room temperature. The slurry was stirred at room temperature for 5 hours, and the product collected by filtration. The wet cake was washed with water-acetonitrile (2:1) (20 mL), and dried under vacuum at 50° C. overnight with a slow flow of nitrogen to give a white solid (1.35 g, 72%). MS-ESI: 467 (M+1), 932 (2M+1); $^1$H-NMR (CDCl$_3$-DMSO-d$_6$) δ 0.95 (3H, t, J=7.4 Hz). 1.13 (9H, s), 1.44 (2H, m), 1.83 (2H, m), 4.50 (2H, t, J=7.4 Hz), 6.85 (1H, s), 7.59 (1H, dd, J=8.5, 2.2 Hz), 7.77 (1H, d, J=5.2 Hz), 7.80 (1H, d, J=8.5 Hz), 8.28 (1H, d, J=2.2 Hz), 8.39 (1H, d, J=5.3 Hz), 8.80 (1H, s); $^{13}$C-NMR (CDCl$_3$-DMSO-d$_6$) δ 13.38, 19.52, 26.17, 29.20, 45.10, 55.56, 114.77, 116.87, 119.83 (q, J=33 Hz, C—CF$_3$), 122.75, 123.48 (q, J=268 Hz, CF$_3$), 127.59, 128.16, 132.46, 132.74, 134.53, 142.44, 163.41, 164.25, 172.13.

Example 6

Preparation of N-[(2Z)-3-butyl[1,3]thiazolo[4,5-c]pyridin-2(3H)-ylidene]-2-{[(2S)-1-methylpyrrolidin-2-yl]methoxy}-5-(trifluoromethyl)benzamide

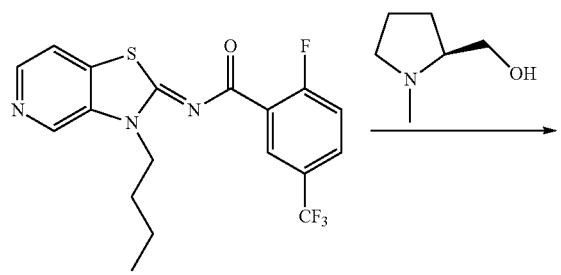

38
-continued

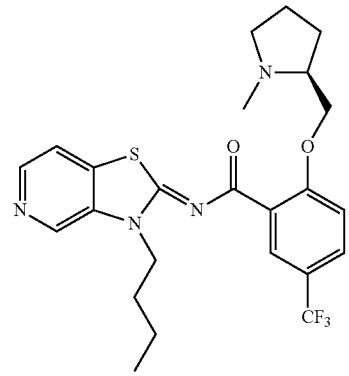

To a 250 mL three-necked flask were charged sodium tert-butoxide (97%, 0.99 g, 10 mmol), and anhydrous tetrahydrofuran (18 mL). The mixture was stirred, and cooled down to about 0° C. A solution of (S)-(1-methylpyrrolidin-2-yl) methanol (1.38 g, 12 mmol) in THF (2.0 mL) was added slowly at the internal temperature <5° C. The solution was mixed at <5° C. for 30 minutes, followed by addition of the product (1.59 g, 4.0 mmol) from Part B of example 1 in tetrahydrofuran (36 mL) at <0° C. The resulting mixture was stirred at about 0° C. for 4 hours or until less than 5% of starting material remains. 65 g of 1.5% $H_3PO_4$ aqueous solution was added slowly to the reaction mixture at <5° C. The resulting slurry was diluted with dichloromethane (100 mL), and mixed at room temperature for 15 minutes. The organic was washed with 20% brine (50 mL), and concentrated to about 20 mL volume, chased with isopropanol (50 mL) to an approximate 20 mL volume under a reduced pressure. The resulting slurry was stirred at room temperature for 1 hour, and the product collected by filtration. The wet cake was dried under vacuum at 50° C. overnight with a slow flow of nitrogen to give a white solid (1.20 g, 60% yield). MS-ESI: 493 (M+1); $^1$H-NMR (CDCl$_3$-DMSO-d$_6$) δ 0.94 (3H, t, J=7.4 Hz), 1.42 (2H, m), 1.68 (3H, m), 1.82 (2H, m), 1.96 (1H, m), 2.23 (1H, m), 2.40 (3H, s), 2.69 (1H, m), 2.96 (1H, m), 4.04 (2H, m), 4.50 (2H, d, J=7.4 Hz), 7.20 (1H, d, J=8.6 Hz), 7.68 (1H, dd, J=8.6, 2.0 Hz), 7.84 (1H, d, J=5.1 Hz), 8.20 (1H, d, J=2.0 Hz), 8.41 (1H, d, J=5.1 Hz), 8.86 (1H, s); $^{13}$C-NMR (CDCl$_3$-DMSO-d$_6$) δ 13.44, 19.50, 22.78, 28.24, 29.25, 41.38, 45.09, 57.16, 63.12, 71.84, 112.96, 117.76, 120.17 (q, J=33 Hz, C—CF$_3$), 123.49 (q, J=269 Hz, C$_{1-3}$), 126.09, 127.51, 128.42, 132.76, 132.76, 134.42, 142.53, 159.72, 164.40, 172.39.

Example 7

N-[(2Z)-1-butyl[1,3]thiazolo[5,4-b]pyridin-2(1H)-ylidene]-2-{[(2R)-2-hydroxypropyl]oxy}-5-(trifluoromethyl)benzamide Part A: Preparation of N-[(2Z)-1-butyl[1,3]thiazolo[5,4-b]pyridin-2(1H)-ylidene]-2-fluoro-5-(trifluoromethyl)benzamide Hydrochloride salt

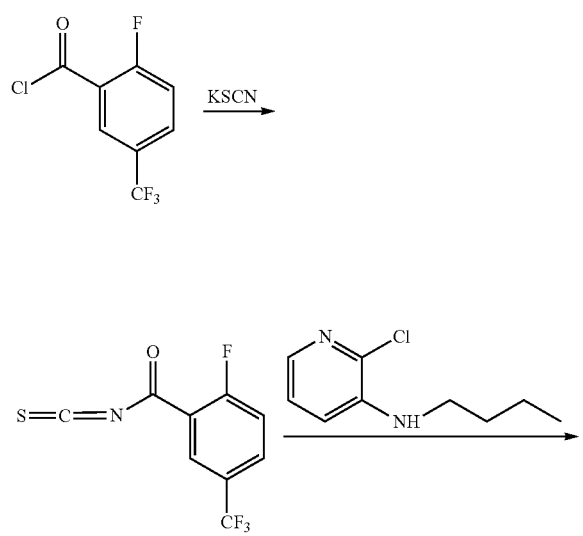

To a three-necked flask were charged potassium thiocyanate (5.0 g, 50.4 mmol), and tetrahydrofuran (110 mL). 2-Fluoro-5-(trifluoromethyl)benzoyl chloride (10.39 g, 41.7 mmol) was added into the flask slowly at room temperature. The reaction mixture was stirred at room temperature for 3 hours or until less than 1% of the acid chloride remains. The reaction mixture was filtered to remove potassium chloride by-product, and rinsed with tetrahydrofuran (10 mL). The combined solution of 2-fluoro-5-(trifluoromethyl)benzoyl isothiocyanate was charged back to the three-necked flask, followed by addition of N-butyl-2-chloropyridin-3-amine (6.91 g, 37.4 mmol) and tetrahydrofuran (100 mL). The reaction mixture was heated to approximately 50° C., and stirred vigorously for 2 days. The product suspension was then cooled to room temperature, and the product collected by filtration. The wet cake was washed with tetrahydrofuran (50 mL), and dried under vacuum at 50° C. to give the desired product (7.83 g, 48% isolated yield). MS-ESI: 398 (M+1); $^1$H-NMR (DMSO-$d_6$) δ 0.96 (3H, t, J=7.4 Hz), 1.42 (2H, m), 1.81 (2H, m), 4.51 (2H, t, J=7.6 Hz), 7.53-7.64 (2H, m), 7.97-8.05 (1H, m), 8.21 (1H, dd, J=8.3, 1.2 Hz), 8.46 (1H, dd, J=6.7, 2.3 Hz), 8.52 (1H, dd, J=4.7, 1.2 Hz).

Part B: Preparation of N-[(2Z)-1-butyl[1,3]thiazolo[5,4-b]pyridin-2(1H)-ylidene]-2-fluoro-5-(trifluoromethyl)benzamide

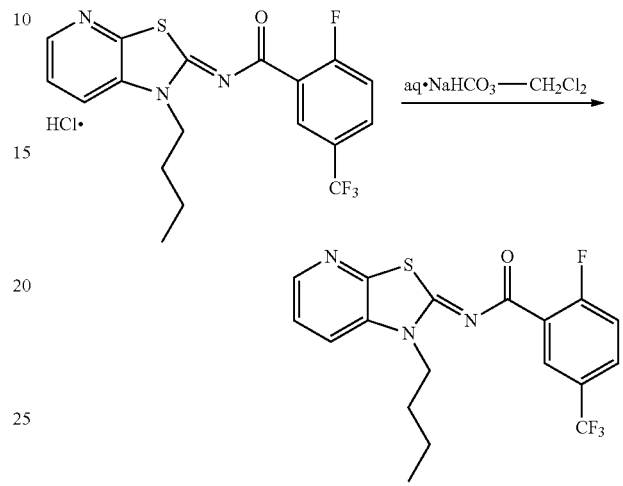

2.03 g of the hydrochloride salt (4.63 mmol) from Part A of Example 7, and dichloromethane (37 mL) were charged to a three-necked flask. 9.47 g of 8% sodium bicarbonate aqueous solution was added into the flask, and the biphasic mixture stirred at room temperature for 2 hours. The aqueous phase was extracted with dichloromethane (10 mL). The organic phases were combined, dried with anhydrous sodium sulfate, filtered, and concentrated under vacuum to 1.69 g (91% isolated yield) of the freebase as a yellow solid.

Part C: N-[(2Z)-1-butyl[1,3]thiazolo[5,4-b]pyridin-2(1H)-ylidene]-2-{[(2S)-2-(methoxymethoxy)propyl]oxy}-5-(trifluoromethyl)benzamide

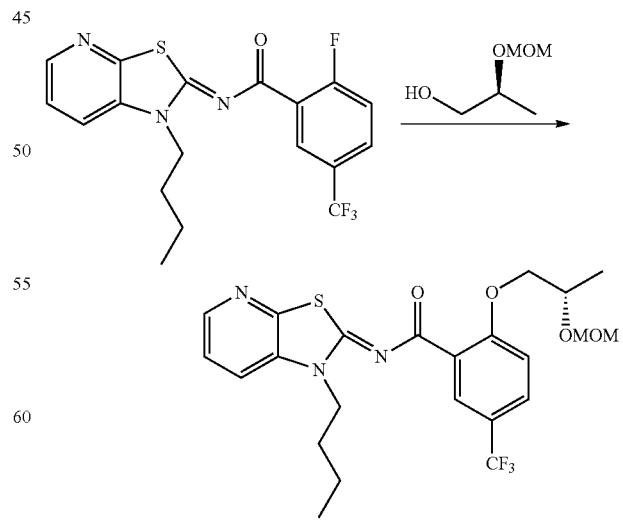

To a 10 mL conical vial were charged sodium tert-butoxide (97%, 84.3 mg, 0.851 mmol), and anhydrous tetrahydrofuran (2 mL). The mixture was stirred, and cooled down to about 0° C. (S)-2-(Methoxymethoxy)propan-1-ol (123 mg, 1.01 mmol) was added slowly at the internal temperature <5° C. The solution was mixed at <5° C. for 45 minutes, followed by addition of the product (199 mg, 0.50 mmol) from Part B of Example 7 in anhydrous tetrahydrofuran (6 mL) at <0° C. The resulting mixture was stirred at about 0° C. for 2 hours or until less than 5% of starting material remains. 16 g of 1.5% $H_3PO_4$ aqueous solution was added slowly to the reaction mixture at <5° C. The resulting slurry was allowed to warm up to room temperature. The slurry was stirred at room temperature for 15 hours, and the product collected by filtration. The wet cake was washed with water (3.5 mL), and dried under vacuum at 50° C. overnight with a slow flow of nitrogen to provide an off-white solid (225 mg, 90% isolated yield). MS-ESI: 498 (M+1); $^1$H-NMR (CDCl$_3$) δ 1.02 (3H, t, J=7.3 Hz), 1.35 (3H, d, J=6.3 Hz), 1.42-1.53 (2H, m), 1.86 (2H, p, J=7.5 Hz), 3.39 (3H, s), 4.00-4.08 (1H, m), 4.16 (1H, dd, J=9.5, 6.7 Hz), 4.19-4.30 (1H, m), 4.43 (2H, t, J=7.4 Hz), 4.73 (1H, d, J=6.7 Hz), 4.85 (1H, d, J=6.7 Hz), 7.07 (1H, d, J=8.7 Hz), 7.36 (1H, dd, J=8.1, 4.8 Hz), 7.55 (1H, dd, J=8.2, 1.4 Hz), 7.66 (1H, dd, J=8.7, 2.5 Hz), 8.41 (1H, d, J=2.4 Hz), 8.47 (1H, dd, J=4.8, 1.3 Hz).

Part D: Preparation of N-[(2Z)-1-butyl[1,3]thiazolo[5,4-b]pyridin-2(1H)-ylidene]-2-{[(2S)-2-hydroxypropyl]oxy}-5-(trifluoromethyl)benzamide

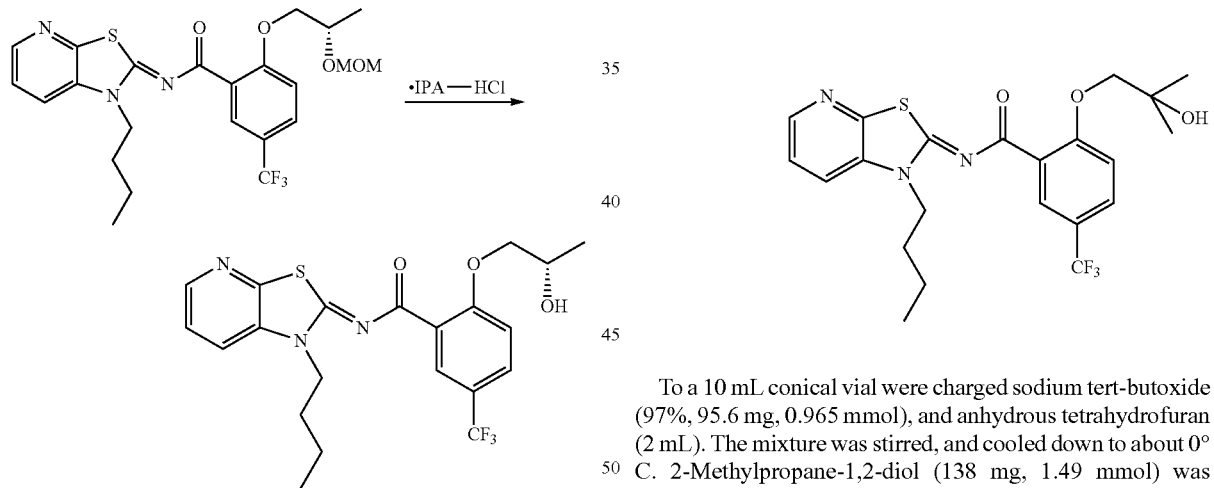

To a 10 mL conical vial were charged the product (203 mg, 0.40 mmol) from Part C of Example 7 and isopropanol (5 mL). The slurry was heated to about 60° C., and concentrated hydrochloric acid solution (0.163 mL) added slowly. The resulting mixture was stirred at 60° C. for 12 hours or until less than 3% of the starting material remains as determined by HPLC. The suspension was cooled down to room temperature, and the product filtered to afford the desired product as a hydrochloride salt. The product was dried under vacuum at 50° C. overnight with a slow flow of nitrogen to give an off-white solid (127 mg, 64% isolated yield). MS-ESI: 454 (M+1); $^1$H-NMR (CDCl$_3$) δ 1.03 (3H, t, J=7.3 Hz), 1.28 (3H, d, J=6.3 Hz), 1.42-1.60 (2H, m), 1.88 (2H, p, J=7.5 Hz), 3.90 (1H, t, J=8.7 Hz), 4.21-4.29 (1H, m), 4.31 (1H, dd, J=9.2, 3.0 Hz), 4.49 (2H, t, J=7.4 Hz), 7.13 (1H, d, J=8.6 Hz), 7.44 (1H, dd, J=8.2, 4.8 Hz), 7.65-7.73 (2H, m), 8.46 (1H, d, J=2.4 Hz), 8.50 (1H, dd, J=4.8, 1.3 Hz).

Example 8

Preparation of N-[(2Z)-1-butyl[1,3]thiazolo[5,4-b]pyridin-2(1H)-ylidene]-2-(2-hydroxy-2-methylpropoxy)-5-(trifluoromethyl)benzamide

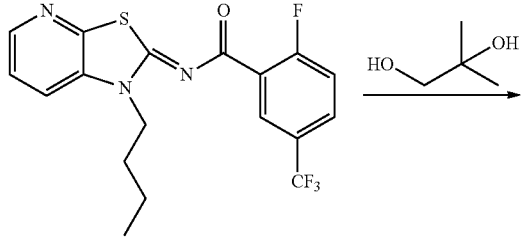

To a 10 mL conical vial were charged sodium tert-butoxide (97%, 95.6 mg, 0.965 mmol), and anhydrous tetrahydrofuran (2 mL). The mixture was stirred, and cooled down to about 0° C. 2-Methylpropane-1,2-diol (138 mg, 1.49 mmol) was added slowly at the internal temperature <5° C. The solution was mixed at <5° C. for 45 minutes This solution was added slowly to a second solution of the product (198 mg, 0.50 mmol) from Part B of Example 7 in anhydrous tetrahydrofuran (6 mL) at <0° C. The resulting mixture was stirred at about 0° C. for 2 hours. 16 g of 1.5% $H_3PO_4$ aqueous solution was added slowly to the reaction mixture at <5° C. The resulting slurry was allowed to warm up to room temperature. The slurry was stirred at room temperature for 48 hours, and the product collected by filtration. The wet cake was recrystallized with water-isopropanol (1:1) (5 mL), and dried under vacuum at 50° C. overnight with a slow flow of nitrogen to give an off-white solid (105 mg, 45% isolated yield). MS-ESI: 468 (M+1); $^1$H-NMR (CDCl$_3$) δ 1.03 (3H, t, J=7.3 Hz). 1.38 (6H, s), 1.44-1.55 (2H, m), 1.82-1.93 (2H, m), 4.03 (2H, s), 4.45 (2H, t, J=7.4 Hz), 4.60 (1H, s), 7.06 (1H, d, J=8.6 Hz),

Example 9

Preparation of N-[(2Z)-1-butyl[1,3]thiazolo-[5,4-b]pyridin-2(1H)-ylidene]-2-{[2S]-1-methylpyrrolidin-2-yl]methoxy}-5-(trifluoromethyl)benzamide

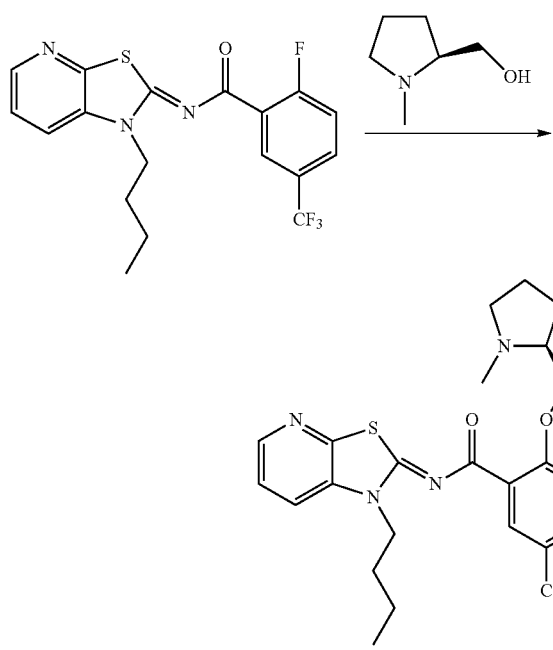

To a 10 mL conical vial were charged sodium tert-butoxide (97%, 87.4 mg, 0.882 mmol), and anhydrous tetrahydrofuran (2 mL). The mixture was stirred, and cooled down to about 0° C. A solution of (S)-(1-methylpyrrolidin-2-yl)methanol (121 mg, 1.01 mmol) was added slowly at the internal temperature <5° C. The solution was mixed at <5° C. for 45 minutes, followed by addition of the product (198 mg, 0.50 mmol) from Part B of example 7 in tetrahydrofuran (6 mL) at <0° C. The resulting mixture was stirred at about 0° C. for 19 hours. 16 g of 1.5% $H_3PO_4$ aqueous solution was added slowly to the reaction mixture at <5° C. The resulting solution was evaporated to approximately one half volume causing the product to precipitate. The resulting slurry was stirred at room temperature for 1 hour, and the product collected by filtration. The wet cake was dried under vacuum at 50° C. overnight with a slow flow of nitrogen to give a pale yellow solid (132 mg, 53% isolated yield). MS-ESI: 493 (M+1); $^1$H-NMR (DMSO-$d_6$) δ 0.95 (3H, t, J=7.1 Hz), 1.42 (2H, m), 1.6-2.2 (6H, m), 2.6 (1H, m), 2.74 (3H, s), 3.4 (2H, m), 4.20 (1H, m), 4.31 (1H, m), 4.47 (2H, d, J=7.1 Hz), 7.36 (1H, d, J=8.8 Hz), 7.58 (1H, dd, J=8.3, 4.8 Hz), 7.85 (1H, dd, J=8.8, 2.3 Hz), 8.15 (1H, dd, J=8.3, 1.3 Hz), 8.26 (1H, d, J=2.2 Hz), 8.50 (1H, dd, J=4.8, 1.2 Hz).

It is understood that the foregoing detailed description and accompanying examples are merely illustrative and are not to be taken as limitations upon the scope of the invention, which is defined solely by the appended claims and their equivalents. Various changes and modifications to the disclosed embodiments can be apparent to those skilled in the art. Such changes and modifications, including without limitation those relating to the chemical structures, substituents, derivatives, intermediates, syntheses, formulations and/or methods of use of the invention, can be made without departing from the spirit and scope thereof.

We claim:
1. A process for preparing a compound of formula (Ib) or (IIIa)

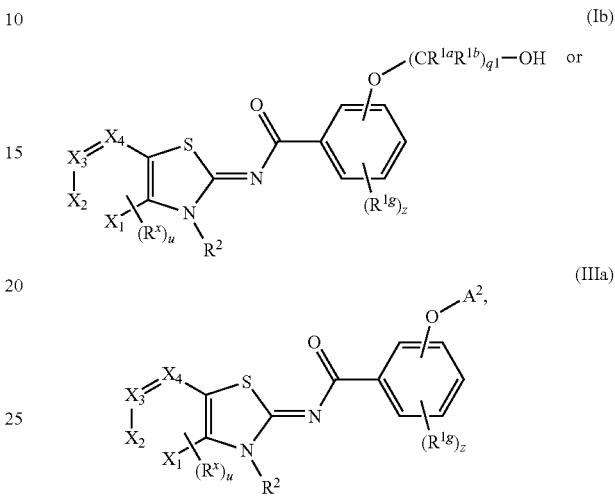

or salt thereof, wherein $R^{1g}$, at each occurrence, is each independently chosen from the group consisting of $G^{1d}$, $C_1$-$C_4$ alkyl, $C_2$-$C_4$ alkenyl, $C_2$-$C_4$ alkynyl, halogen, $C_1$-$C_4$ haloalkyl, —CN, —OR$^f$, —OC(O)R$^f$, —OC(O)N(R$^f$)$_2$, —S(O)$_2$R$^e$, —S(O)$_2$N(R$^f$)$_2$, —C(O)R$^f$, —C(O)OR$^f$, —C(O)N(R$^f$)$_2$, —N(R$^f$)$_2$, —N(R$^f$)C(O)R$^f$, —N(R$^f$)S(O)$_2$R$^e$, —N(R$^f$)C(O)O(R$^e$), —N(R$^f$)C(O)N(R$^f$)$_2$, —(CR$^{1c}$R$^{1d}$)$_{q3}$—OR$^f$, —(CR$^{1c}$R$^{1d}$)$_{q3}$—OC(O)R$^f$, —(CR$^{1c}$R$^{1d}$)$_{q3}$—OC(O)N(R$^f$)$_2$, —(CR$^{1c}$R$^{1d}$)$_{q3}$—S(O)$_2$R$^e$, —(CR$^{1c}$R$^{1d}$)$_{q3}$—S(O)$_2$N(O$_2$, —(CR$^{1c}$R$^{1d}$)$_{q3}$—C(O)R$^f$, —(CR$^{1c}$R$^{1d}$)$_{q3}$—C(O)OR$^f$, —(CR$^{1c}$R$^{1d}$)$_{q3}$—C(O)N(R$^f$)$_2$, —(CR$^{1c}$R$^{1d}$)$_{q3}$—N(R$^f$)$_2$, —(CR$^{1c}$R$^{1d}$)$_{q3}$—N(R$^f$)C(O)R$^f$, —(CR$^{1c}$R$^{1d}$)$_{q3}$—N(R$^f$)S(O)$_2$R$^e$, —(CR$^{1c}$R$^{1d}$)$_{q3}$—N(R$^f$)C(O)O(R$^e$), —(CR$^{1c}$R$^{1d}$)$_{q3}$—N(R$^f$)C(O)N(R$^f$)$_2$, and —(CR$^{1c}$R$^{1d}$)$_{q3}$—CN;

R$^e$, at each occurrence, is independently $C_1$-$C_4$ alkyl, $C_1$-$C_4$ haloalkyl, monocyclic cycloalkyl, or —(CR$^{1c}$R$^{1d}$)$_{q3}$-(monocyclic cycloalkyl);

R$^f$, at each occurrence, is independently hydrogen, $C_1$-$C_4$ alkyl, $C_1$-$C_4$ haloalkyl, —(CR$^{1c}$R$^{1d}$)$_{q3}$—OR$^g$, monocyclic cycloalkyl, or —(CR$^{1c}$R$^{1d}$)$_{q3}$-(monocyclic cycloalkyl);

R$^g$, at each occurrence, is independently hydrogen, $C_1$-$C_4$ alkyl, $C_1$-$C_4$ haloalkyl, monocyclic cycloalkyl, or —(CR$^{1c}$R$^{1d}$)$_{q3}$-(monocyclic cycloalkyl);

$A^2$ is N(R$^b$)(R$^c$), $G^{1c}$, or —(CR$^{1a}$R$^{1b}$)$_q$-$G^{1c}$;

$G^{1c}$ is a monocyclic heterocycle or a monocyclic cycloalkyl wherein each ring is optionally substituted with 1, 2, 3, or 4 substituents independently selected from the group consisting of oxo, alkyl, alkenyl, alkynyl, halogen, haloalkyl, —CN, alkoxy, haloalkoxy, —C(O)OH, and —C(O)O(alkyl);

$R^2$ is $C_2$-$C_{10}$ alkyl, alkenyl, alkynyl, haloalkyl, —(CR$^{2a}$R$^{2b}$)$_{q4}$—O—R$^a$, —(CR$^{2a}$R$^{2b}$)$_{q4}$—O—$G^{2a}$, —(CR$^{2a}$R$^{2b}$)$_{q4}$—O(CR$^{2c}$R$^{2d}$)$_{q5}$-$G^{2a}$, —(CR$^{2a}$R$^{2b}$)$_{q5}$—C(O)—R$^a$, —(CR$^{2a}$R$^{2b}$)$_{q5}$—C(═N—OR$^e$)R$^a$, —(CR$^{2a}$R$^{2b}$)$_{q5}$—SO$_2$—R$^d$, —(CR$^{2a}$R$^{2b}$)$_{q5}$-$G^{2a}$, —(CR$^{2a}$R$^{2b}$)$_{q5}$—C(O)N(R$^b$)(R$^c$), —(CR$^{2a}$R$^{2b}$)$_{q4}$—OC(O)N(R$^b$)(R$^c$), or —(CR$^{2a}$R$^{2b}$)$_{q5}$—CN;

G$^{2a}$, at each occurrence, is independently cycloalkyl, cycloalkenyl, heterocycle, aryl, or heteroaryl; wherein each of the rings as represented by G$^{2a}$ is optionally substituted with 1, 2, 3, 4, or 5 substituents independently selected from the group consisting of oxo, alkyl, halogen, hydroxy, alkoxy, haloalkoxy, and haloalkyl;

R$^a$ and R$^c$, at each occurrence, are each independently hydrogen, alkyl, haloalkyl, —(CR$^{1a}$R$^{1b}$)$_{q2}$—OR$^h$, —(CR$^{1a}$R$^{1b}$)$_{q2}$—N(R$^h$)$_2$, G$^{1d}$, or —(CR$^{1a}$R$^{1b}$)$_{q2}$G$^{1d}$;

R$^b$, at each occurrence, is independently hydrogen, alkyl, haloalkyl, alkoxyalkyl, monocyclic cycloalkyl, —(CR$^{1c}$R$^{1d}$)$_{q2}$-(monocyclic cycloalkyl), or haloalkoxyalkyl;

R$^d$, at each occurrence, is independently alkyl, haloalkyl, —(CR$^{1a}$R$^{1b}$)$_{q2}$—OR$^h$, —(CR$^{1a}$R$^{1b}$)$_{q2}$—N(R$^h$)$_2$, G$^{1d}$, or —(CR$^{1a}$R$^{1b}$)$_{q2}$-G$^{1d}$;

G$^{1d}$, at each occurrence, is independently a monocyclic heterocycle, a monocyclic heteroaryl, a phenyl, a monocyclic cycloalkyl, or a monocyclic cycloalkenyl; each of which is optionally substituted with 1, 2, 3, or 4 substituents independently selected from the group consisting of —N(R)$_2$, —CN, oxo, alkyl, haloalkyl, alkoxy, haloalkoxy, halogen, and hydroxy;

R$^h$, at each occurrence, is independently hydrogen, C$_1$-C$_4$ alkyl, C$_1$-C$_4$ haloalkyl, monocyclic cycloalkyl, or —(CR$^{1c}$R$^{1d}$)$_{q3}$-(monocyclic cycloalkyl)

wherein the monocyclic cycloalkyl, as a substituent or part of a substituent, of R$^b$, R$^e$, R$^f$, R$^g$, and R$^h$, at each occurrence, is independently unsubstituted or substituted with 1, 2, 3, or 4 substituents independently selected from the group consisting of C$_1$-C$_4$ alkyl, halogen, oxo, hydroxy, C$_1$-C$_4$ alkoxy, C$_1$-C$_4$ haloalkoxy, and C$_1$-C$_4$ haloalkyl;

q, q1, and q2, at each occurrence, are each independently 1, 2, 3, or 4;

R$^{1a}$, R$^{1b}$, R$^{1c}$, R$^{1d}$, R$^{2a}$, R$^{2b}$, R$^{2c}$, and R$^{2d}$, at each occurrence, are each independently hydrogen, halogen, C$_1$-C$_4$ alkyl, or C$_1$-C$_4$ haloalkyl;

q3, at each occurrence, is independently 1, 2 or 3;

q4, at each occurrence, is independently 2, 3, 4, or 5;

q5, at each occurrence, is independently 1, 2, 3, 4, 5, or 6;

z is 0, 1, 2, 3, or 4;

one of X$_1$, X$_2$, X$_3$, and X$_4$ is N and the others are CH;

u is 0, 1, 2, or 3; and each R$^x$ is an optional substituent on any substitutable carbon atom, and is independently selected from the group consisting of alkyl, halogen, hydroxy, alkoxy, haloalkoxy, and haloalkyl; comprising the steps of (1a) treating a compound of formula (IV)

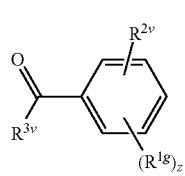

(IV)

wherein R$^{2v}$ is halogen or sulfonate; and R$^{3v}$ is halogen or OH; with a thiocyanate source to produce a compound of formula (V)

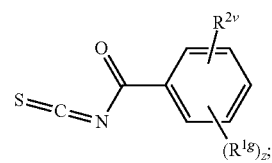

(V)

(1b) reacting a compound of formula (V) with a compound of formula (VI)

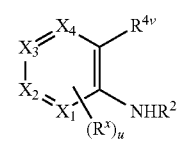

(VI)

wherein R$^{4v}$ is halogen or sulfonate to produce a compound of formula (II) or a salt thereof

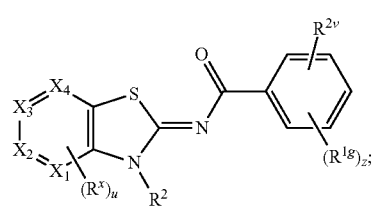

(II)

(2a) treating a compound of formula (II) or a salt thereof with a compound of formula HO—(CR$^{1a}$R$^{1b}$)$_{q1}$—O—R$^p$ or HO-A$^2$, or a salt thereof, wherein R$^p$ is hydrogen or a hydroxy-protecting group; to produce a compound of formula (IIIa) or (IIIb), or a salt thereof

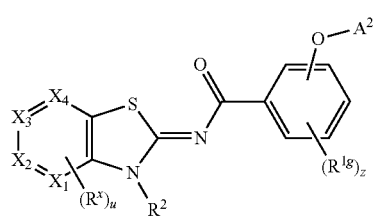

(IIIa)

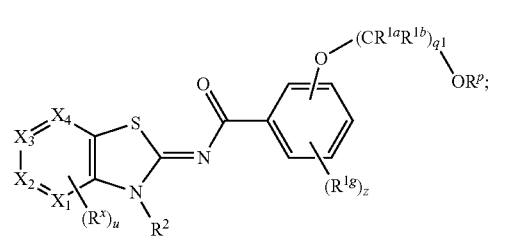

(IIIb)

(2b) deprotect a compound of formula (IIIb) or a salt thereof wherein R$^p$ is a hydroxy-protecting group to form a compound of formula (Ib) or a salt thereof

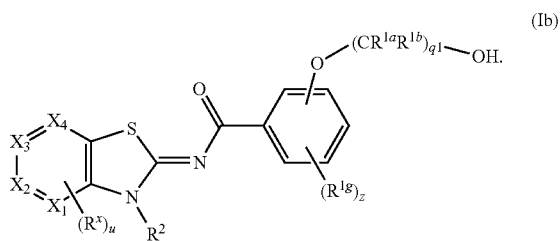

2. A process for preparing a compound of formula (Ib) or (IIIa)

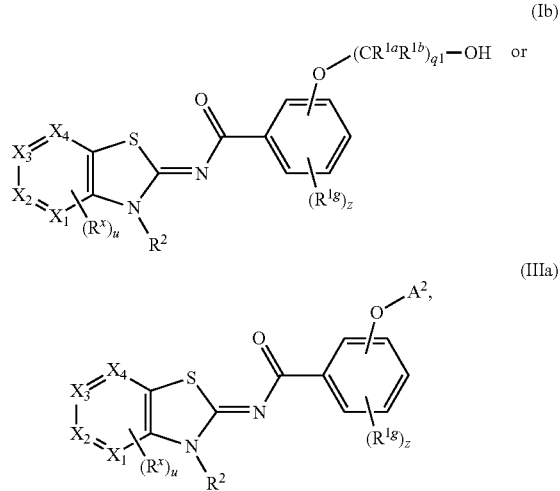

or a salt thereof, wherein $R^{1g}$, at each occurrence, is each independently chosen from the group consisting of $G^{1d}$, $C_1$-$C_4$ alkyl, $C_2$-$C_4$ alkenyl, $C_2$-$C_4$ alkynyl, halogen, $C_1$-$C_4$ haloalkyl, —CN, —$OR^f$, —$OC(O)R^f$, —$OC(O)N(R^f)_2$, —$S(O)_2R^e$, —$S(O)_2N(R^f)_2$, —$C(O)R^f$, —$C(O)OR^f$, —$C(O)N(R^f)_2$, —$N(R^f)_2$, —$N(R^f)C(O)R^f$, —$N(R^f)S(O)_2R^e$, —$N(R^f)C(O)O(R^e)$, —$N(R^f)C(O)N(R^f)_2$, —$(CR^{1c}R^{1d})_{q3}$—$OR^f$, —$(CR^{1c}R^{1d})_{q3}$—$OC(O)R^f$, —$(CR^{1c}R^{1d})_{q3}$—$C(O)N(R^f)_2$, $(CR^{1c}R^{1d})_{q3}$—$S(O)_2R^e$, —$(CR^{1c}R^{1d})_{q3}$—$S(O)_2N(O)_2$, —$(CR^{1c}R^{1d})_{q3}$—$C(O)R^f$, —$(CR^{1c}R^{1d})_{q3}$—$C(O)OR^f$, —$(CR^{1c}R^{1d})_{q3}$—$C(O)N(O)_2$, —$(CR^{1c}R^{1d})_{q3}$—$N(R^f)_2$, —$(CR^{1c}R^{1d})_{q3}$—$N(R^f)C(O)R^f$, —$(CR^{1c}R^{1d})_{q3}$—$N(R^f)S(O)_2R^e$, —$(CR^{1c}R^{1d})_{q3}$—$N(R^f)C(O)O(R^e)$, —$(CR^{1c}R^{1d})_{q3}$—$N(R^f)C(O)N(R^f)_2$, and —$(CR^{1c}R^{1d})_{q3}$—CN;

$R^e$, at each occurrence, is independently $C_1$-$C_4$ alkyl, $C_1$-$C_4$ haloalkyl, monocyclic cycloalkyl, or —$(CR^{1c}R^{1d})_{q3}$-(monocyclic cycloalkyl);

$R^f$, at each occurrence, is independently hydrogen, $C_1$-$C_4$ alkyl, $C_1$-$C_4$ haloalkyl, —$(CR^{1c}R^{1d})_{q3}$—$OR^g$, monocyclic cycloalkyl, or —$(CR^{1c}R^{1d})_{q3}$— (monocyclic cycloalkyl);

$R^g$, at each occurrence, is independently hydrogen, $C_1$-$C_4$ alkyl, $C_1$-$C_4$ haloalkyl, monocyclic cycloalkyl, or —$(CR^{1c}R^{1d})_{q3}$-(monocyclic cycloalkyl);

$A^2$ is $N(R^b)(R^c)$, $G^{1c}$, or —$(CR^{1a}R^{1b})_q$-$G^{1c}$;

$G^{1c}$ is a monocyclic heterocycle or a monocyclic cycloalkyl wherein each ring is optionally substituted with 1, 2, 3, or 4 substituents independently selected from the group consisting of oxo, alkyl, alkenyl, alkynyl, halogen, haloalkyl, —CN, alkoxy, haloalkoxy, —C(O)OH, and —C(O)O(alkyl);

$R^2$ is $C_2$-$C_{10}$ alkyl, alkenyl, alkynyl, haloalkyl, —$(CR^{2a}R^{2b})_{q4}$—O—$R^a$, —$(CR^{2a}R^{2b})_{q4}$—O-$G^{2a}$, —$(CR^{2a}R^{2b})_{q4}$—O—$(CR^{2c}R^{2d})_{q5}$-$G^{2a}$, (—$CR^{2a}R^{2b})_{q5}$—C(O)—$R^a$, —$(CR^{2a}R^{2b})_{q5}$—C(=N—$OR^e$)$R^a$, —$(CR^{2a}R^{2b})_{q5}$—$SO_2$—$R^d$, —$(CR^{2a}R^{2b})_{q5}$-$G^{2a}$, —$(CR^{2a}R^{2b})_{q5}$—C(O)N($R^b$)($R^c$), —$(CR^{2a}R^{2b})_{q4}$—OC(O)N($R^b$)($R^c$), or —$(CR^{2a}R^{2b})_{q5}$—CN;

$G^{2a}$, at each occurrence, is independently cycloalkyl, cycloalkenyl, heterocycle, aryl, or heteroaryl; wherein each of the rings as represented by $G^{2a}$ is optionally substituted with 1, 2, 3, 4, or 5 substituents independently selected from the group consisting of oxo, alkyl, halogen, hydroxy, alkoxy, haloalkoxy, and haloalkyl;

$R^a$ and $R^c$, at each occurrence, are each independently hydrogen, alkyl, haloalkyl, —$(CR^{1a}R^{1b})_{q2}$—$OR^h$, —$(CR^{1a}R^{1b})_{q2}$—$N(R^h)_2$, $G^{1d}$, or —$(CR^{1a}R^{1b})_{q2}$-$G^{1d}$;

$R^b$, at each occurrence, is independently hydrogen, alkyl, haloalkyl, alkoxyalkyl, monocyclic cycloalkyl, —$(CR^{1c}R^{1d})_{q2}$-(monocyclic cycloalkyl), or haloalkoxyalkyl;

$R^d$, at each occurrence, is independently alkyl, haloalkyl, —$(CR^{1a}R^{1b})_{q2}$—$OR^h$, —$(CR^{1a}R^{1b})_{q2}$—$N(R^h)_2$, $G^{1d}$, or —$(CR^{1a}R^{1b})_{q2}$-$G^{1d}$;

$G^{1d}$, at each occurrence, is independently a monocyclic heterocycle, a monocyclic heteroaryl, a phenyl, a monocyclic cycloalkyl, or a monocyclic cycloalkenyl; each of which is optionally substituted with 1, 2, 3, or 4 substituents independently selected from the group consisting of —$N(R)_2$, —CN, oxo, alkyl, haloalkyl, alkoxy, haloalkoxy, halogen, and hydroxy;

$R^h$, at each occurrence, is independently hydrogen, $C_1$-$C_4$ alkyl, $C_1$-$C_4$ haloalkyl, monocyclic cycloalkyl, or —$(CR^{1c}R^{1d})$-(monocyclic cycloalkyl)

wherein the monocyclic cycloalkyl, as a substituent or part of a substituent, of $R^b$, $R^e$, $R^f$, $R^g$, and $R^h$, at each occurrence, is independently unsubstituted or substituted with 1, 2, 3, or 4 substituents independently selected from the group consisting of $C_1$-$C_4$ alkyl, halogen, oxo, hydroxy, $C_1$-$C_4$ alkoxy, $C_1$-$C_4$ haloalkoxy, and $C_1$-$C_4$ haloalkyl;

q, q1, and q2, at each occurrence, are each independently 1, 2, 3, or 4;

$R^{1a}$, $R^{1b}$, $R^{1c}$, $R^{1d}$, $R^{2a}$, $R^{2b}$, $R^{2c}$, and $R^{2d}$, at each occurrence, are each independently hydrogen, halogen, $C_1$-$C_4$ alkyl, or $C_1$-$C_4$ haloalkyl;

q3, at each occurrence, is independently 1, 2 or, 3;

q4, at each occurrence, is independently 2, 3, 4, or 5;

q5, at each occurrence, is independently 1, 2, 3, 4, 5, or 6;

z is 0, 1, 2, 3, or 4;

one of $X_1$, $X_2$, $X_3$, and $X_4$ is N and the others are CH;

u is 0, 1, 2, or 3; and each $R^x$ is an optional substituent on any substitutable carbon atom, and is independently selected from the group consisting of alkyl, halogen, hydroxy, alkoxy, haloalkoxy, and haloalkyl; comprising the steps of (2a) treating a compound of formula (II)

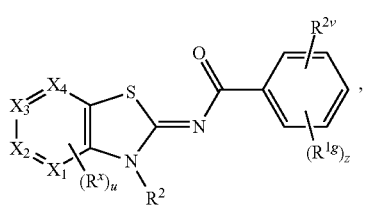

or a salt thereof with a compound of formula HO—($CR_{1a}R^{1b}$)$_{q1}$—O—$R^p$ or HO-$A^2$, or a salt thereof, wherein $R^p$ is hydrogen or a hydroxy-protecting group; to produce a compound of formula (IIIa) or (IIIb), or a salt thereof

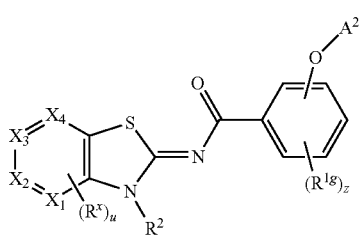

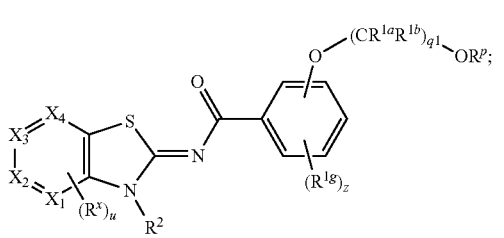

(2b) deprotect a compound of formula (IIIb) or a salt thereof wherein $R^p$ is a hydroxy-protecting group to produce a compound of formula (Ib) or a salt thereof

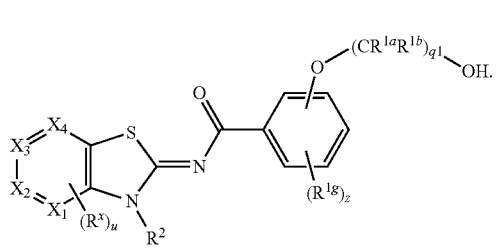

3. The process according to claim 1 further comprising quenching the reaction in step (2a) with the addition of an acid.

4. The process according to claim 3 wherein the acid is phosphoric acid, acetic acid, hydrochloric acid, or sulfuric acid.

5. The process according to claim 3 wherein the acid is phosphoric acid.

6. The process according to claim 1 wherein a strong base is present in the reaction of step (2a).

7. The process according to claim 6 wherein the strong base is sodium or potassium tert-butoxide.

8. The process according to claim 1 wherein the thiocyanate in step (1a) source is sodium or potassium thiocyanate.

9. The process according to claim 1 wherein the reaction of step (2a) is conducted in a solvent selected from the group consisting of tetrahydrofuran, acetonitrile, 1,4-dioxane, toluene, and N,N-dimethylformamide.

10. The process according to claim 1 wherein $R^p$ in step (2a) is a hydroxy-protecting group.

11. The process according to claim 10 wherein $R^p$ is alkoxyalkyl.

12. The process according to claim 1 wherein $R^p$ in step (2a) is hydrogen.

13. The process according to claim 1 wherein $R^{2v}$ is halogen.

14. The process according to claim 1 wherein $R^{3v}$ is Cl, and $R^{4v}$ is Cl or Br.

15. The process according to claim 1 wherein $R^2$ is $C_2$-$C_{10}$ alkyl.

16. The process according to claim 15 wherein $X_2$ is N and $X_1$, $X_3$, and $X_4$ are CH.

17. The process according to claim 1 wherein the hydroxy group of $(CR^{1a}R^{1b})_{q1}OH$ is a secondary or tertiary hydroxy.

18. The process according to claim 17 wherein $R^2$ is $C_2$-$C_{10}$ alkyl.

* * * * *